(12) United States Patent
Cadavid et al.

(10) Patent No.: US 9,717,453 B2
(45) Date of Patent: Aug. 1, 2017

(54) COGNITIVE COMPOSITE PARAMETERS AND USES THEREOF FOR EVALUATING MULTIPLE SCLEROSIS

(71) Applicant: BIOGEN MA INC., Cambridge, MA (US)

(72) Inventors: Diego Cadavid, Concord, MA (US); David Erlanger, New York, NY (US); John DeLuca, Rockaway, NJ (US); Ralph Benedict, Buffalo, NY (US); Frederick W. Foley, River Edge, NJ (US); Jeffrey A. Wilken, Fairfax, VA (US)

(73) Assignee: BIOGEN IDEC MA INC., Cambridge, MA (US)

( * ) Notice: Subject to any disclaimer, the term of this patent is extended or adjusted under 35 U.S.C. 154(b) by 0 days.

(21) Appl. No.: 14/395,802

(22) PCT Filed: Apr. 19, 2013

(86) PCT No.: PCT/US2013/037329
§ 371 (c)(1),
(2) Date: Oct. 20, 2014

(87) PCT Pub. No.: WO2013/158969
PCT Pub. Date: Oct. 24, 2013

(65) Prior Publication Data
US 2015/0110741 A1 Apr. 23, 2015

Related U.S. Application Data

(60) Provisional application No. 61/636,291, filed on Apr. 20, 2012.

(51) Int. Cl.
*A61B 5/16* (2006.01)
*G09B 5/06* (2006.01)
*G06F 19/00* (2011.01)
*G09B 19/00* (2006.01)

(52) U.S. Cl.
CPC ............... *A61B 5/168* (2013.01); *A61B 5/16* (2013.01); *G06F 19/345* (2013.01); *G06F 19/3431* (2013.01); *G09B 5/06* (2013.01); *G09B 19/00* (2013.01)

(58) Field of Classification Search
None
See application file for complete search history.

(56) References Cited

U.S. PATENT DOCUMENTS 5,840,299 A 11/1998 Bendig et al.
2004/0167380 A1 8/2004 Simon
2015/0220693 A1 8/2015 Cadavid et al.

FOREIGN PATENT DOCUMENTS

WO 2006/060787 A2 6/2006
WO 2009111886 A1 9/2009
WO 2011133799 A1 10/2011
WO 2014028299 A1 2/2014

OTHER PUBLICATIONS

Boringa et al., The Brief Repeatable Battery of Neuropsychological Tests: normative values allow application in multiple sclerosis clinical practice, 2001, Multiple Sclerosis 7: 263-267.*
Parmenter et al., Screening for cognitive impairment in multiple sclerosis using the Symbol Digit Modalities Test, 2007, Multiple Sclerosis 13: 52-57.*
Tombaugh, T.N., A comprehensive review of the Paced Auditory Serial Addition Test (PASAT), Archives of Clinical Neuropsychology 21:53-76.*
Paramenter et al., "The utility of regression-based norms in interpreting the minimal assessment of cognitive function in multiple sclerosis (MACFIMS)" Journal of Interntional Neurospsychological Society (2010) 16(1):6-16.
Paty et al., "interferon beta-1b is effective in relapsing-remitting multiple sclerosis. II. MRI analysis results of a multicenter, randomized, double-blind, placebo-controlled trial" Neurology (1993)43:662-667.
Pepinsky et al "improved Pharmacokinetic Properties of a Polyethylene Glycol-Modified Form of Interferon-B-1a with Preserved in Vitro Bioactivity" The Journal of Pharmacology and Experimental Therapeutics (2001) 297 (3):1059-1066.
Peterson et al.: "VCAM-1-Positive Microglia Target Oligodendrocytes at the Border of Multiple Sclerosis Lesions" Journal of Neuropathology and Experimental Neurology (2002) 61(6):539-546.
Peyser et al., "Cognitive Function in Patients with multiple Sclerosis" Arch Neurol (1980) 37(9).577-579.
Polman et al., "The Multiple Sclerosis Functional Composite—A clinically meaningful meaningful measure of disability" Neurology (2010) 74(Supplement 3): S8-S15.
Poser et al., "New Diagnostic Criteria for Multiple Sclerosis: Guidelines for Research Protocols" Annals of Neurology (1983) 13(3):227-231.
Prakash et al,: "Cognitive impairments in relapsing-remitting multiple sclerosis; a meta-analysis" Mult. Scler. (2008) 14:1250-1261.
Pulido et al., "Functional Evidence for Three Distinct and Idependently Inhibitable Adhesion Activities Mediated by the Human Integrin VLA-4" The Journal of Biological Chemistry (1991) 266(16):10241-10245.
Rao et al., "Cognitive dysfunction in multiple sclerosis. I. Frequency, patterns, and prediction" Neurology (1991) 41 (5):685-691.
Rao et al., "Cognitive dysfunction in multiple sclerosis: ll. Impact on employment and social functioning" Neurology (1991) 41(5):692-696.

(Continued)

*Primary Examiner* — John Ulm
(74) *Attorney, Agent, or Firm* — Lando & Anastasi, LLP

(57) ABSTRACT

Methods, systems and kits for the identification, assessment and/or treatment of a subject having multiple sclerosis are disclosed.

20 Claims, 7 Drawing Sheets

(56) References Cited

OTHER PUBLICATIONS

Rao et al., "Neuropsychology of multiple sclerosis" Current Opinion in Neurology (1995) 8(3).216-220.
Sanchez-Madrid et al., "VLA-3: A novel polypeptide association within the VLA molecular complex: cell distribution and biochemical characterization" European Journal of Immunology (1986) 16(11):1343-1349.
Sipe et al., "A neurologic rating scale (NRS) for use in multiple sclerosis" Neurology (1984) 34(10):1368.
Stankiewicz et al., "Brain MRI Lesion Load at 1.5T and 3T versus Clinical Status in Multiple Sclerosis" J Neuroimaging (2011) 21:e50-e56.
Strober et al., "Sensitivity of conventional memory tests in multiple sclerosis: comparing the Rao Brief Repeatable Neuropsychological Battery and the Minimal Assessment of Cognitive Function in MS" Mult, Scler, (2009) 15 (9)1077-1084.
Tekok-Kilic et al , "Independent contributions of cortical gray matter atrophy and ventricle enlargement for predicting neuropsychological impairment in multiple sclerosis" J. NeuroImage (2007) 36:1294-1300.
Thornton et al., "Memory Impairment in Multiple Sclerosis: A Quantitative Review" Neuropsychology (1997) 11 (3):357-366.
Trapp et al., "Axonal Transection in the Lesions of Multiple Sclerosis" The New England Journal of Medicine (1998) 338(5):278-285.
Wallin of al., "Cognitive dysfunction in multiple sclerosis: Assessment, imaging and risk factors" Journal of Rehabilitation Research and Development (2006) 43(1):63-72.
Wishart et al , "Neuropsychological Aspects of Multiple Sclerosis: A Quantative Review" Journal of Clinical and Experimental Neuropsychology (1997) 19(6):810-824.
Written Opinion of the International Searching Authority for PCT/US2013/037329. mailed Jul. 16, 2013.
Arduini et al., "Expression, purification, and characterization of rat interferon-beta, and preparation of an N-terminally PEGylated form with improved pharmacokinetic parameters" Protein Expr (2004) 34(2):229-242.
Baker, et al., "N-Terminally PEGylated Human Interferon-beta-1a with Improved Pharmacokinetic Properties and in Vivo Efficacy in a Melanoma Angiogenesis Model" Bioconjugate Chem (2006) 17(1):179-188.
Baker, et al., "PEGylated Interferon Beta—1a: Meeting an Unmet Medical Need in the Treatment of Relapsing Multiple Sclerosis" J Interferon Cytokine Res (2010) 30(10):777-785.
Benedict et al, "Revision of the Brief Visuospatial Memory Test. Studies of normal performance, reliability, and validity." Psychological Assessment (1996) 8:145-153.
Benedict et al., "An attempt at memory retraining in severe amnesia: An experimental single-case study" Neuropsychological Rehabilitation: An International Journal (1993) 3(1):37-51.
Benedict et al., "Diffusion-weighted imaging predicts cognitive impairment in multiple sclerosis" Mult Scler. (2007) 13:722-730.
Benedict et al., "Effects of using same—versus alternate—form memory tests during short-interval repeated assessments in multiple sclerosis" Journal of International Neuropsychological Society (2005) 11:727-736.
Benedict et al., "Minimal Neuropsychological Assesment of MS Patients. A Consensus Approach" The Clinical Neuropsychologist (2002) 16(3):381-397.
Benedict et al., "Neocortical Atrophy. Third Ventricular Width, and Cognitive Dysfunction in Multiple Sclerosis" Arch Neurol. (2006) 63:1301-1306.
Benedict et al., "Preliminary standardization of a new visuospatial memory test with six alternate forms" The Clinical Neuropsychologist (1995) 9(1):11-16.
Benedict et al., "Repeated assessment of neuropsychological deficits in multiple sclerosis using the Symbol Digit Modalities Test and the MS Neuropsychological Screening Questionnaire" Mult. Scler. (2008) 14:904-946.
Benedict of ai., "Screening for multiple sclerosis cognitice impairment using a self-administered 15-item questionnaire" Multiple Sclerosis (2003) 9(1):95-101.
Benedict et al., "Validity of the minimal assessment of cognitive function in multiple sclerosis (MACFIMS)" Journal of International Neuropsychological Society (2006) 12(4):549-558.
Bitsch et al., "Acute axonal injury in multiple sclerosis—Correlation with demyelination and inflammation" Brain (2000) 123:1174-1183.
Bjartmar et al., "Axonal and neuronal degeneration in multiple sclerosis: mechanisms and functional consequences" Current Opinion Neural (2001) 14(3)271-278.
Bjartmar et al., "Axonal pathology in myelin disorders" Journal of Neurocytology (1999) 28:383-395.
Bornstein et al.. "A Pilot Trial of Cop 1 in Exacerbating-Remitting Multiple Sclerosis" New England Journal of Medicine (1987) 317:408-414.
Buschke et al., "Evaluating storage, retention, and retrieval in disordered memory and learning" Neurology (1974) 24:1019-1025.
Cadavid et al., "Clinical consequences of MRI activity in treated multiple sclerosis" Multiple Sclerosis (2011) 17:1113-1121.
Chang et al., "Premyelinating Oligodendrocytes in Chronic Lesions of Multiple Sclerosis" N Engl J Med (2002) 346 (3)165-173.
Chiaravalloti et al., "Cognitive impairment in multiple sclerosis" The Lancet Neurology (2008) 7(12):1139-1151.
Christodoulou et al., "Cognitive performance and MR markers of cerebreal injury in cognitively impaired MS patients" Neurology (2003) 60:1793-1798.
DeLoire et al., "Cognitive impairment as marker of diffuse brain abnormalities in early relapsing remitting multiple sclerosis" J Neurol. Neurosurg, Psychiatry (2005) 76:519-526.
DeLuca et al., "Is Speed of Processing or Working Memory the Primary Information Processing Deficit in Multiple Sclerosis" Journal of Clinical and Experimental Neuropsychology (204) 26(4):550-562.
Drake at al., "Psychometrics and normative data for the Multiple Sclerosis Functional Composite: replacing the PASAT with the Symbol Digit Modalaties Test" Mult Scler (2010) 16:228-237.
Duda et al., "Glatiramer acetate (Copaxone) induces degenerate, Th2-polarized immune responses in patients with multiple sclerosis" J. Clin, Invest. (2000) 105:967-976.
Ferguson et al., "Axonal damage in acute multiple sclerosis lesions" Brain (1997) 120:393-399.
Fischer et al., "Neuropsychological effects of interferon Beta—1a in relapsing multiple sclerosis" Annals of Neurology (2000) 48(6)885-892.
Fischer et al., "What Do We Really Know About Cognitive Dysfunction, Affective Disorders, and Stress in Multiple Sclerosis? A Practitioner's Guide" Neurorehabil Neural Repair (1994) 8:151-164.
Frohman at al., "The utility of MRI in suspected MS: Report of the Therapeutics and Technology Assessment Subcommittee of the American Academy of Neurology" Neurology (2003) 61(5):602-611.
Gilewski et al., "The Memory Functioning Questionnaire for assessment of memory complaints in adulthood and old age" Psychology and Aging (1990) 5(4):482-490.
Gronwall et al., "Paced Auditory Serial-Addition Task: A Measure of Recovery from Concussion" Perceptual and Motor Skills (1977) 44(2) 367-373.
Hannay at al., "Selective reminding test: An examination of the equivalence of four forms" Journal of Clinical and Experimental Neuropsychology (1985) 7(3).251-263.
Heesen et al., "Correlates of cognitive dysfunction in multiple sclerosis" Brain, Behavior and Immunity (2010) 24 (7):1148-55.
Hemler at al., "Characterization of the cell surface heterodimer VLA-4 and related peptides" The Journal of Biological Chemistry (1987) 262:11478-11485.
Houtchens et al., "Thalamic atrophy and cognition in multiple sclerosis" Neurology (2007) 69(12):1213-1223.
International Preliminary Report on Patentability with Written Opinion for PCT/US2013/037829, issued Oct. 21, 2014.

(56) References Cited

OTHER PUBLICATIONS

International Search Report for PCT/US2013/037329, mailed Jul. 23, 2013.

Issekutz et al., "Effect of a new monoclonal antibody, TA-2, that inhibits lymophocyte adherence to cytokine stimulated endothelium in the rat" J Immunol (1991) 147 (1):109-116.

Jonsson, et al., "Cognitive impairment in newly diagnosed multiple sclerosis patients: A 4-year follow-up study", Journal of Neurological Sciences (2006) 245(1-2):77-85.

Kornek at al., "Multiple Sclerosis and Chronic Autoimmune Encephalomyelitis" American Journal Pathology (2000) 157(267-276).

Kurtzke et al., "Clinical definition for multiple sclerosis treatment trials" Annals of Neurology (1994) 36.S73-S79.

Kurtzke at al., "Rating neurologic impairment in multipte sclerosis: An expanded disability status scale (EDSS)" Neurology (1983) 33:1444-1452.

Langdon et al., "Recommendations for a Brief International Cognitive Assessment for Multiple Sclerosis (BICAMS)" Mult. Scler. (2012) 18(6):891-898.

Lee et al., "Spotlight on Fumarates" The International MS Journal (2008) 15:12-18.

Lyon-Caen at al., "Cognitive Function in Recent-Onset Demyelinating Diseases" Arch. Neurol. (1986)43 (11 ):1138-1141.

McDonald at al., "Are magnetic resonance findings predictive of clinical outsome in therapeutic trials in multiple sclerosis? The dilemma of interferon-Beta" Ann. Neurol. (1994) 36(1):14-18.

McDonald et al.: "Recommended Diagnostic Criteria for Multiple Sclerosis: Guidelines from the International Panel on the Diagnosis of Multiple Sclerosis" Ann. Neurol, (2001) 50:121-127.

Morrow et al., "Erratum to: Effects of acute relapses on neuropsychological status in multiple sclerosis patients" J Neurol (2011) 258:1609.

Nicholas et al., "Development of oral immunomodulatory agents in the management of mutitple sclerosis" Drug Design Development and Therapy (2011) 5:255-274.

Chris H. Polman et al: "The Multiple Sclerosis Functional Composite—A clinically meaningful measure of disability", Neurology, vol. 74(17_Supplement_3) Supplement 3, New Frontiers in Multiple Sclerosis: Impact of Disease-Modifying Therapies on Nontraditional Measures of Disease Activity, Apr. 27, 2010 (Apr. 27, 2010), pp. S8-S17, KP055071466, Retrieved from the Internet: <URL:http://patients.aan.com/resources/neurologynow/index.cfm?event=home.articlePDF&id=ovid.com:/bib/ovftdb/00006114-201004273-00003>.

Francois Bethoux et al: "Evaluating Walking in Patients with Multiple Sclerosis", International Journal of MS Care, vol. 13, No. 1, Jun. 1, 2011 (Jun. 1, 2011), pp. 4-14, XP055090329, ISSN: 1537-2073, DOI: 10.7224/1537-2073-13.1.4.

Gaspari M et al: "Refining an Automatic EDSS Scoring Expert System for Routine Clinical Use in Multiple Sclerosis", IEEE Transactions on Information Technology in Biomedicine, IEEE Service Center, Los Alamitos, CA, US, vol. 13, No. 4, Jul. 1, 2009 (Jul. 1, 2009), pp. 501-511, XP011345557, ISSN: 1089-7771, DOI: 10.1109/TITB.2008.926498.

International Search Report for corresponding PCT Application No. PCT/US2013/054128 dated Dec. 5, 2013.

\* cited by examiner

A

B

COGNITIVE COMPOSITE PARAMETERS AND USES THEREOF FOR EVALUATING MULTIPLE SCLEROSIS

RELATED APPLICATIONS

This application is the U.S. National Phase Application of 35 U.S.C. §371 of International Application No. PCT/2013/037329, filed Apr. 19, 2013, which claims the benefit of U.S. Provisional Application No. 61/636,291, filed Apr. 20, 2012, the contents of each of which are incorporated herein by reference in their entirety.

BACKGROUND OF THE INVENTION

Multiple sclerosis (MS) is an inflammatory disease of the brain and spinal cord characterized by recurrent foci of inflammation that lead to destruction of the myelin sheath. In many areas, nerve fibers are also damaged. Inflammatory activity in MS patients tends to be highest in the initial phase of disease.

Data have demonstrated that irreversible axonal loss occurs early in the course of MS. Transected axons fail to regenerate in the central nervous system (CNS); and therefore, early treatment aimed at suppressing MS lesion formation is of significant importance. As early as disease onset, axons are transected in lesions with active inflammation (Trapp et al. (1998) *N Engl J Med* 338: 278-285; Bjartmar et al. (2001) *Curr Opin Neurol* 14: 271-278; Ferguson et al. (1997) *Brain* 120: 393-399). The degree of demyelination is related to the degree of inflammation and the exposure of demyelinated axons to the inflammatory environment, as well as non-inflammatory mediators (Trapp et al. (1998) *N Engl J Med* 338: 278-285; Kornek et al. (2000) *Am J Pathol* 157: 267-276; Bitsch et al. (2000) *Brain* 123: 1174-1183). There is also destruction of oligodendrocytes with impaired remyelination in demyelinating lesions (Peterson et al. (2002) *J Neuropathol Exp Neurol* 61: 539-546; Chang et al. (2002) *N Engl J Med* 346: 165-173). The loss of oligodendrocytes leads to a reduction in the capacity to re-myelinate and may result in the loss of trophic factors that support neurons and axons (Bjartmar et al. (1999) *J Neurocytol* 28: 383-395).

MS-mediated damage to the brain and spinal cord causes not only physical disabilities, but also significant cognitive impairment. Despite the significant impact that cognitive impairments have on the overall disability and quality of life of MS patients, adequate tools for the assessment of MS-associated cognitive impairments are needed. Current test batteries for assessment of cognitive impairment often require a panel of lengthy, cumbersome tests many of which are not pertinent to the disease itself and that require administration and interpretation by trained neuropsychologists.

Therefore, there is a need to establish a practical and valid cognitive measurement tool for use in MS patient evaluation, which are not only tailored to assess the cognitive domains affected by MS, but are also efficient, and easily administered with cross-cultural utility.

SUMMARY OF THE INVENTION

The present invention provides, at least in part, methods, systems and kits for the identification, assessment and/or treatment of a subject having a neurological disorder, e.g., multiple sclerosis (MS). In one embodiment, the methods, systems and kits include the step of detecting and/or quantifying a cognitive impairment in the subject (e.g., an MS patient), by obtaining a composite cognitive endpoint that includes a measure of processing speed and a measure of learning and memory (referred to herein as an "attention factor" and a "memory factor," respectively). Composite cognitive endpoints offer several advantages over current methodologies, including, but not limited to, increased sensitivity, enhanced statistical power, smaller sampling size and enhanced simplicity. The invention can, therefore, be used, for example, for one or more of: (i) diagnosing, prognosing and/or evaluating, a subject (e.g., an MS patient); (ii) evaluating responsiveness to, or monitoring, a therapy (e.g., an MS therapy); (iii) identifying a patient as being stable, or showing improvement or disease progression; (iv) to stratify a subject (e.g., an MS patient or patient population) as being a disease non-progressor or a disease progressor; and/or (v) more effectively monitoring, treating multiple sclerosis, or preventing worsening of disease and/or relapses.

Accordingly, in one aspect, the invention features a method of evaluating (e.g., evaluating and/or quantifying cognitive function or impairment in) a subject (e.g., a patient, a patient group or a patient population), having a neurological disorder (e.g., multiple sclerosis (MS)), or at risk of developing the neurological disorder. The method includes acquiring a value of a composite parameter from the subject, said composite parameter including an attention factor and a memory factor, thereby evaluating the subject. In one embodiment, the subject has MS, e.g., is an MS patient who has undergone or is undergoing treatment with one or more MS therapies.

In a related aspect, the invention features a method of detecting and/or quantifying a cognitive impairment in a subject (e.g., a patient, a patient group or a patient population), having multiple sclerosis (MS), or at risk of developing MS. The method includes acquiring a value of a composite parameter from the subject, said composite parameter including an attention factor and a memory factor, e.g., a first value for attention and/or processing speed (PS) factor and a second value for a memory factor, thereby detecting and/or quantifying the cognitive impairment in the subject. In one embodiment, the subject has MS, e.g., is an MS patient who has undergone or is undergoing treatment with an MS therapy (e.g., one or more MS therapies). The cognitive impairment tested and/or quantified can be used in making treatment decisions.

In some embodiments, responsive to a determination of the value of the composite parameter using the aforesaid methods, the method further includes one or more of the following:

(i) identifying the subject as being in need of a therapy, e.g., an MS therapy (e.g., a first MS therapy or a second (alternative) MS therapy);

(ii) identifying the subject as having an increased or a decreased response to a therapy, e.g., an MS therapy (e.g., a first MS therapy or a second (alternative) MS therapy);

(iii) identifying the subject as being stable, showing an improvement in cognitive abilities (e.g., as being a disease non-progressor), or showing a decline in cognitive abilities (e.g., as being a disease progressor);

(iv) diagnosing, and/or prognosing the subject;

(v) determining a therapy (e.g., an MS therapy), e.g., selecting or altering the course of, a therapy or treatment, a dose, a treatment schedule or time course, and/or the use of an alternative MS therapy);

(vi) determining a time course of disease progression (e.g., MS disease progression) in the subject; and/or (vii) administering a therapy, e.g., an MS therapy (e.g., a first MS therapy or a second (alternative) MS therapy) to the subject).

In one embodiment, one or more of (i)-(vii) are effected in response to the value of the composite parameter. A change (e.g., an increased or a decrease) in the value of the composite parameter relative to a specified parameter indicates one or more of: identifies the subject as being in need of the therapy (e.g., an MS therapy (e.g., a first MS therapy or a second (alternative) MS therapy); identifies the subject as having an increased or decreased response to the therapy; determines the treatment to be used; and/or determines or predicts the time course of the disease (e.g., the MS disease).

In one embodiment, an increase in the value of the composite parameter, relative to the specified parameter, is indicative of improved cognitive function (or decreased cognitive impairment) in the subject.

In one embodiment, a decrease in the value of the composite parameter, relative to the specified parameter, is indicative of decreased cognitive function (or increased cognitive impairment) in the subject.

In another aspect, the invention features a method for identifying a subject (e.g., a patient, a patient group or population), having MS, or at risk for developing MS, as having an increased or a decreased response to an MS therapy. The method includes acquiring a value of a composite parameter from the subject, said composite parameter including an attention factor and a memory factor, e.g., a first value for attention and/or processing speed (PS) factor and a second value for a memory factor, and responsive to said value, identifying the subject having MS, or at risk for developing MS, as being responsive or less responsive to the MS therapy.

In one embodiment, the method includes comparing the value of the composite parameter to a specified parameter (e.g., a reference value as described herein).

In one embodiment, a decreased value of the composite parameter relative to a specified parameter indicates that the subject is less responsive to the MS therapy. For example, a value of at least 0.2, 0.3, 0.4, 0.5, 0.6, 0.7, 0.8, 0.9, 1.0, 1.1, 1.2, 1.3, 1.4, or 1.5 SD, lower than the specified parameter indicates that the subject has increased cognitive impairment, and thus the subject is being less responsive to the MS therapy.

In one embodiment, a decreased value of the composite parameter of at least 0.5 SD relative to a specified parameter indicates that the subject has experienced a cognitive impairment (e.g., a clinically significant cognitive impairment). Such subject can be at risk of experiencing significant disability.

In one embodiment, a decreased value of the composite parameter of at least 1.0 SD relative to a specified parameter indicates that the subject has experienced a cognitive impairment (e.g., a clinically significant cognitive impairment). Such subject can have developed significant disability.

In other embodiments, a stable or increased value of the composite parameter relative to a specified parameter indicates that the subject is stable or has improved cognitive function, and thus the subject is being responsive to the MS therapy.

In other embodiments, an increased value beyond that of the expected practice effect on the composite parameter indicates that the subject has restoration of damaged cognitive function. In certain embodiments, the subject with said increased value can be responsive to a reparative MS therapy (e.g. a remyelinating CNS agent).

In another aspect, the invention features a method of evaluating or monitoring an MS therapy in a subject (e.g., a patient, a patient group or population), having MS, or at risk for developing MS. The method includes:

acquiring a value (e.g., a baseline value) of a composite parameter from the subject, said composite parameter including an attention factor and a memory factor, e.g., a first value for attention and/or processing speed (PS) factor and a second value for a memory factor, and (optionally) responsive to said value, treating, selecting and/or altering one or more of the course of the MS therapy, the dosing of the MS therapy, the schedule or time course of the MS therapy, or administration of a second, alternative MS therapy.

In one embodiment, the method includes comparing the value of the composite parameter to a specified parameter (e.g., a reference value as described herein). In certain embodiments, the sample is obtained at different time intervals, e.g., prior to, during, or after treatment with the MS therapy.

In one embodiment, a decreased value of the composite parameter relative to a specified parameter indicates that the subject is progressing in the disorder. For example, a value of at least 0.2, 0.3, 0.4, 0.5, 0.6, 0.7, 0.8, 0.9, 1.0, 1.1, 1.2, 1.3, 1.4, or 1.5 SD, lower than the specified parameter indicates that the subject has increased cognitive impairment, thus showing disease progression.

In other embodiments, a stable or an increased value of the composite parameter relative to a specified parameter indicates that the subject is stable or has an improved prognosis and/or outcome to the MS therapy.

The method can be used, e.g., to evaluate the suitability of, or to choose between alternative treatments, e.g., a particular dosage, mode of delivery, time of delivery.

In yet another aspect, the invention features a method of evaluating a subject's prognosis or MS disease progression, in a subject (e.g., a patient, a patient group or population), having MS, or at risk for developing MS. The method can be a diagnostic or prognostic method. The method includes:

acquiring a value of a composite parameter from the subject, said composite parameter including an attention factor and a memory factor, e.g., a first value for attention and/or processing speed (PS) factor and a second value for a memory factor, thereby evaluating the subject; and (optionally) comparing the value of the composite parameter to a specified parameter (e.g., a reference value as described herein).

In certain embodiments, the sample is obtained at different time intervals, e.g., prior to, during, and/or after treatment with the MS therapy.

In one embodiment, a decreased value of the composite parameter relative to a specified parameter indicates that the subject is progressing in the disorder. For example, a value of at least 0.2, 0.3, 0.4, 0.5, 0.6, 0.7, 0.8, 0.9, 1.0, 1.1, 1.2, 1.3, 1.4, or 1.5 SD, lower than the specified parameter indicates that the subject has increased cognitive impairment, thus showing disease progression.

In other embodiments, a stable or an increased value of the composite parameter relative to a specified parameter indicates a stable or improved diagnosis or prognosis of the subject.

In other embodiments, any of the aforesaid methods further include treating, or preventing in, a subject having MS one or more symptoms associated with MS. In certain embodiments, the treatment includes reducing, retarding, or preventing, a relapse, or the worsening of a disability, in the MS subject. In one embodiment, the method includes, responsive to the value of the composite parameter, administering to the subject a therapy for MS (also referred to herein as an "MS therapy" or "MS treatment"), in an amount sufficient to reduce one or more symptoms associated with MS.

In yet another aspect, the invention features a method of treating or preventing one or more symptoms associated with MS, in a subject having MS, or at risk for developing MS. The method includes:

acquiring a value of a composite parameter from the subject, said composite parameter including an attention factor and a memory factor, e.g., a first value for attention and/or processing speed (PS) factor and a second value for a memory factor;

responsive to said value, performing one or more of:
administering to a subject an MS therapy, in an amount sufficient to reduce one or more symptoms associated with MS;

selecting and/or altering a dosing of an MS therapy;
selecting and/or altering the schedule or time course of an MS therapy;
selecting and/or administering an alternative MS therapy;
selecting and/or administering a therapy for cognitive and/or memory impairment (e.g., administering one or more of: an agent that increases the level of neurotransmitters in the brain, NMDA receptor agents, and/or CNS stimulants (e.g., dextro or levo amphetamines); and/or
selecting and/or administering a therapy for improving attention and/or processing speed, thereby treating or preventing MS in the subject.

In certain embodiments, in response to an increased value of said composite parameter relative to a reference value, the MS treatment is initiated or continued; and in response to a decreased value of said composite parameter relative to a reference value, the MS treatment is modified (e.g., an alternative MS therapy is used).

In certain embodiments, the MS therapy comprises one or more of an IFN-β1 molecule; a polymer of four amino acids found in myelin basic protein, e.g., a polymer of glutamic acid, lysine, alanine and tyrosine (e.g., glatiramer (Copaxone®)); an antibody or fragment thereof against alpha-4 integrin (e.g., natalizumab (Tysabri®)); an anthracenedione molecule (e.g., mitoxantrone (Novantrone®); or fingolimod (FTY720; Gilenya®); a dimethyl fumarate (e.g., an oral dimethyl fumarate (BG-12)); an antibody to the alpha subunit of the IL-2 receptor of T cells (e.g., Daclizumab); a reparative therapy; an anti-LINGO-1 antibody; or an inhibitor of a dihydroorotate dehydrogenase (e.g., teriflunomide).

In one embodiment, the IFNβ1 molecule is an IFN-β1a agent (e.g., Avonex®, Rebif®). In another embodiment, the IFNβ1 molecule is an INF-β1b agent (e.g., Betaseron®, Betaferon®).

In another embodiment, the IFN-β1 molecule comprises one or more of an IFN-β1a or IFN-β1b polypeptide, a variant, a homologue, a fragment or a derivative thereof (e.g., a pegylated variant thereof).

In one embodiment, the MS therapy includes an antibody or fragment thereof against alpha-4 integrin (e.g., natalizumab (Tysabri®)).

In certain embodiments, the method of treatment includes administration of an MS therapy (e.g., a first MS therapy). In another embodiment, the MS therapy is a second or an alternative therapy (e.g., a therapy selected when a patient is less responsive or shows disease progression when treated with the first therapy).

In one embodiment, the first therapy is chosen from one or more of:

an IFNβ agent (e.g., an IFN-β1a molecule or an IFN-β1b molecule, including analogues and derivatives thereof (e.g., pegylated variants thereof));

a polymer of four amino acids found in myelin basic protein, e.g., a polymer of glutamic acid, lysine, alanine and tyrosine (e.g., glatiramer (Copaxone®));

an antibody against CD52 (e.g., alemtuzumab (Lemtrada®)); or an inhibitor of a dihydroorotate dehydrogenase (e.g., teriflunomide).

In certain embodiments, the MS therapy is an alternative or second therapy to the first MS therapy. In one embodiment, the alternative therapy includes an antibody or fragment thereof against alpha-4 integrin (e.g., natalizumab (Tysabri®)). In yet other embodiments, the alternative therapy includes an anthracenedione molecule (e.g., mitoxantrone (Novantrone®)). In yet another embodiment, the alternative therapy includes a fingolimod (e.g., FTY720; Gilenya®). In one embodiment, the alternative therapy is a dimethyl fumarate (e.g., an oral dimethyl fumarate (BG-12)). In other embodiments, the alternative therapy is an antibody to the alpha subunit of the IL-2 receptor of T cells (e.g., Daclizumab). In another embodiment, the alternative therapy includes a reparative therapy. In yet another embodiment, the alternative therapy includes an anti-LINGO-1 antibody. In one embodiment, the alternative therapy includes an inhibitor of a dihydroorotate dehydrogenase (e.g., teriflunomide).

In certain embodiments, the method further includes the use of one or more symptom management therapies, such as antidepressants, analgesics, anti-tremor agents, among others.

In other embodiments, the method includes step of administering the use of one or more therapies for management of cognitive and/or memory impairment. Examples of such therapies include, but are not limited to, agents that increase the level of neurotransmitters in the brain, NMDA receptor agents, and CNS stimulants such as dextro- or levo-amphetamines.

Additional embodiments or features of any of the foregoing methods are as follows:

Value of Composite Parameter

In certain embodiments, the value of the composite parameter used in the methods and systems described herein is compared to a specified parameter (e.g., a reference value, such as value obtained from at least one of: a healthy subject or an average of healthy subjects; the subject at different time intervals (e.g., prior to, during, or after the MS therapy); a group of MS patients having the same or different disease progressions; the group of MS patients having the same or different disease progressions at different time intervals; a group of MS patients undergoing different MS treatments than the subject; or a group of MS patients undergoing the same MS treatment as the subject. In certain embodiments, the subject is monitored in one or more of the following periods: prior to beginning of treatment; during the treatment; after the treatment has been administered; or at a first and second time points at least 1, 2, 3, 4, 5, or 6 months apart.

In one embodiment, the specified parameter, e.g., the reference value is 0. The value of the composite parameter can range from −0.1 to −2 in a subject with MS.

In one embodiment, an increase in the value of the composite parameter, relative to the specified parameter, is indicative of improved cognitive function in the subject. For example, an increase in the value of the composite parameter, relative to the reference value, by at least 5%, 10%, 20%, 30%, 40%, 50%, or 0.2 to 1.5 SD, or more is indicative of improved cognitive function in the subject.

In another embodiment, a decrease in the value of the composite parameter, relative to the specified parameter, is indicative of decreased cognitive function in the subject. For example, a value of at least 0.2, 0.3, 0.4, 0.5, 0.6, 0.7, 0.8, 0.9, 1.0, 1.1, 1.2, 1.3, 1.4, or 1.5 SD, lower than, the specified parameter indicates that the subject has increased cognitive impairment. In other embodiments, a decrease in the value of the composite parameter, relative to the reference value, by at least 5%, 10%, 20%, 30%, 40%, 50%, or 0.2 to 1.5 SD, or more is indicative of decreased cognitive function in the subject. In certain embodiments, a composite value of −1.5 or −1.0 SD below a reference value is indicative of cognitive impairment.

In certain embodiments, the value of the composite parameter is different in subjects with different MS diagnoses. For example, the value of the composite parameter is higher in an MS patient having relapse remitting multiple sclerosis (RRMS) compared to an MS patient with secondary progressive multiple sclerosis (SPMS).

In certain embodiments, the value of the composite parameter is indicative of cognitive function in a domain including one or more of information processing speed, information processing efficiency, visual memory, verbal memory (e.g., memory acquisition), executive function or perceptual processing.

In one embodiment, the value of the composite parameter is acquired by evaluating one, two, three, four or more attention and memory factors.

Memory factors can include one or more verbal or visual memory factors.

Exemplary tests for evaluating memory factors include, but are not limited to, tests for evaluating one or more of auditory memory, verbal learning and/or remembering visual information (e.g., Selective Reminding Test (SRT)); tests for evaluating auditory/verbal memory (e.g., California Verbal Learning Test Second Edition (CVLT2)), or the Rey Auditory Verbal Learning Test (RAVLT); and tests for evaluating visual/spatial memory (e.g., Brief Visuospatial Memory Test Revised (BVMT-R)).

Exemplary tests for evaluating attention, e.g., processing speed and/or working memory, include but are not limited to, tests for evaluating one or more of working memory, processing speed (e.g., auditory information processing speed), flexibility or calculation ability (e.g., Paced Auditory Serial Addition Test (PASAT)); and tests for evaluating complex scanning and/or visual tracking (e.g., Symbol Digit Modalities Test (SDMT)).

In certain embodiments, the attention and memory factors are obtained by administering one, two, three, four or more of:

(i) an assessment of processes involved in learning and/or remembering visual information (e.g., Selective Reminding Test (SRT)), (ii) an assessment of visuospatial memory (e.g., Brief Visual/spatial Memory Test (BVMT)), (iii) an assessment of complex scanning and/or visual tracking (e.g., Symbol Digit Modalities Test (SDMT), or (iv) an assessment of one or more of auditory information processing speed, flexibility or calculation ability (e.g., Paced Auditory Serial Addition Test (PASAT)).

The assessments described herein can be administered simultaneously or within the same evaluation interval in the subject. In some embodiments, the evaluation interval refers to two or more assessments administered at two or more time points to obtain the value of the composite parameter.

Z Scores/Factor Construction

In certain embodiments, the value of the composite parameter used in the methods described herein is an average value of one or more memory factors and one or more attention factors.

In certain embodiments, the value of the composite parameter includes a first value for an attention and/or processing speed (PS) factor and a second value for a memory factor, wherein:

(i) the first value is acquired by obtaining a score, e.g., a standardized score, from at least two assessments indicative of attention and/or processing speed, and (ii) the second value is acquired by obtaining a score, e.g., a standardized score, from at least one assessment of auditory/verbal learning and memory, and at least one assessment of visual learning and memory.

In some embodiments, the first value is obtained by one or more of:

(i) averaging the scores from at least one assessment of complex scanning and/or visual tracking, and at least one or two assessment(s) of processing speed, flexibility and/or calculation ability;

(ii) as a function of a score based on a Symbol Digit Modalities Test (SMDT)) and a score based on at least one or two Paced Auditory Serial Addition Test (PASAT); or (ii) calculating the first value using the following equation:

{SMDT score+[PASAT 3 score+PASAT 2 score]/2)}/2.

In some embodiments, the second value is obtained by one or more of:

(i) averaging the scores from at least one or two assessments indicative of verbal learning and delayed recall, combined with at least one or two assessments indicative of visual learning and delayed recall;

(ii) averaging the scores at least one or two components of a Selective Reminding Test (SRT) and at least one or two components of a Brief Visuospatial memory Test (BVMT); or (iii) calculating the second value using the following equation:

[SRT learning score+SRT delay score+BVMT learning score and BVMT delay score]/4.

The first and the second values can be weighed equally (e.g., 50:50) in generating the value of the composite parameter, or differentially, e.g., said first or second value being about 10%, 20%, 25%, 30%, 40%, 60%, 75% or more the value of the other value, in generating the value of the composite parameter.

In yet other embodiments, the scores from the assessments used to obtain the second value are weighed equally, or differentially, e.g., said first or second value being about 10%, 20%, 25%, 30%, 40%, 60%, 75% or more the value of the other value, in generating the value of the composite parameter.

In other embodiments, the scores from the assessments of verbal and visual memory are weighed equally, or differentially as described herein. The scores from the assessments of learning and delayed recall components can be weighed equally or differentially as described herein.

In yet other embodiments, the scores from the at least one assessment of complex scanning and/or visual tracking, and the at least one or two assessment(s) of processing speed, flexibility and/or calculation ability are weighed equally, or differentially, e.g., said first or second value being about 10%, 20%, 25%, 30%, 40%, 60%, 75% or more the value of the other value, in generating the value of the composite parameter.

In one embodiment, the value of the attention factor is evaluated by a obtaining a score of the average of the sum of an assessment of complex scanning and/or visual tracking and the average of at least two assessments of auditory information processing speed, flexibility or calculation ability; or {SMDT+[PASAT 3+PASAT 2]/2)}/2.

In other embodiments, the value of the verbal memory factor is evaluated by a obtaining a score of the average of the sum of at least two assessments of processes involved in learning and/or remembering visual information; or (SRT Total Learning+SRT Delayed Recall)/2.

In yet other embodiments, the value of the visual memory factor is evaluated by a obtaining a score of the average of at least two assessments of visuospatial memory; or (BVMT Total Recall+BVMT Delayed Recall)/2.

In other embodiments, the value of the memory factor is the average of the value of the verbal memory factor and the visual memory factor.

In other embodiments, the value of the composite parameter has a reliability of at least 0.65, 0.69, 0.70, 0.75, 0.80, 0.85, 0.90 or higher.

In other embodiments, the scores used to generate the composite are adjusted, e.g., demographically adjusted, thus providing a standardized score.

In other embodiments, the value of the composite parameter comprises a score value chosen from one or more of: −0.6 to −1.6 for SDMT, −0.2 to −1.2 for PASAT 3, −0.12 to −1.12 for PASAT 2, −0.25 to −1.25 for SRT Total, −0.3 to −1.3 for SRT Delay, −0.8 to −1.8 for BVMT-R Total, or −1.2 to −2.2 for BVMTR Delay.

Subjects

For any of the methods disclosed herein, the subject treated, or the subject from which the value is obtained, is a subject having, or at risk of having MS at any stage of treatment. In certain embodiments, the MS patient is chosen from a patient having one or more of: Benign MS, RRMS (e.g., quiescent RRMS, active RRMS), primary progressive MS, or secondary progressive MS. In one embodiment, the subject is asymptomatic. In other embodiments, the subject has one or more MS-like symptoms, such as those having clinically isolated syndrome (CIS) or clinically defined MS (CDMS). In one embodiment, the subject is an MS patient (e.g., a patient with RRMS or SPMS) prior to administration of an MS therapy described herein. In one embodiment, the subject is a newly diagnosed or an undiagnosed RRMS or SPMS patient. In another embodiment, the subject is an MS patient (e.g., an RRMS patient) after administration of an MS therapy described herein. In other embodiments, the subject is an MS patient after administration of the MS therapy for one, two weeks, one month, two months, three months, four months, six months, one year or more.

In certain embodiments, the subject is a patient having one of: benign MS; relapse/remitting MS (RRMS, e.g., quiescent RRMS, active RRMS); primary progressive MS; secondary progressive MS (SPMS); clinically isolated syndrome (CIS); or clinically defined MS (CDMS). In one embodiment, the subject has RRMS (e.g., quiescent RRMS, active RRMS). In other embodiments, the subject has secondary progressive MS (SPMS).

The methods described herein can be used to distinguish MS patients, e.g., to distinguish between RRMS and SPMS.

Timing of Assessment

In one embodiment, the methods described herein include comparing the value of the composite parameter to a specified parameter (e.g., a reference value as described herein). A value can be analyzed at any stage of treatment, for example, prior to, during, or after terminating, administration of the MS therapy, to thereby determine appropriate dosage(s) and MS therapy (e.g., amount per treatment or frequency of treatments) for prophylactic or therapeutic treatment of the subject. In certain embodiments, the methods include the step of acquiring the value of the composite parameter from the subject, prior to, or after, administering the MS therapy, to the subject.

In one embodiment, the value of the composite parameter is assessed at pre-determined intervals, e.g., a first point in time and at least at a subsequent point in time. For example, the first and subsequent time points are evaluated at least about 1, 2, 3, 4, 5, 6, 7, 8, 9, 10, 11, or 12 months apart; e.g., typically between 1 to 8, 2 to 7, 3 to 6, months apart.

In one embodiment, a time course is measured by determining the time between significant events in the course of a patient's disease, wherein the measurement is predictive of whether a patient has a long time course. In another embodiment, the significant event is the progression from primary diagnosis to death. In another embodiment, the significant event is the progression from primary diagnosis to worsening disease. In another embodiment, the significant event is the progression from primary diagnosis to relapse. In another embodiment, the significant event is the progression from secondary MS to death. In another embodiment, the significant event is the progression from remission to relapse. In another embodiment, the significant event is the progression from relapse to death. In certain embodiments, the time course is measured with respect to one or more overall survival rate, time to progression and/or using the EDSS or other assessment criteria.

In one embodiment, the value of the composite parameter is assessed in an MS patient prior to administration of an MS therapy described herein. For example, the value of the composite parameter is assessed in a newly diagnosed MS patient. In another embodiment, the value of the composite parameter is assessed in an MS patient after administration of an MS therapy described herein (e.g., after administration of the MS therapy for one, two weeks, one month, two months, three months, four months, six months, one year or more).

In certain embodiments, a pre-determined measure or value is created after evaluating the sample by dividing subject's samples into at least two patient subgroups (e.g., progressors vs. non-progressors). In certain embodiments, the number of subgroups is two, such that the patient sample is divided into a subgroup of patients having a specified value of the composite parameter described herein, and a subgroup not having the specified value of the composite parameter. In certain embodiments, the number of subgroups is greater than two, including, without limitation, three subgroups, four subgroups, five subgroups and six subgroups, depending on stratification of predicted MS therapy efficacy as correlated with particular value of the composite parameter.

In one embodiment, the subject is treated with a first MS therapy (e.g., an interferon, glatiramer (Copaxone®), Daclizumab), and shows a value in the range of responsiveness described herein (thus, indicating that the subject evaluated is responsive to the first MS therapy). A value in the range of non-responsiveness described herein indicates that the subject evaluated is less responsive to the first MS therapy, and thus, an alternative, second MS therapies can be considered, including, but not limited to, natalizumab (Tysabri®), mitoxantrone (Novantrone®), fingolimod (FTY720; Gilenya®), dimethyl fumarate (e.g., an oral dimethyl fumarate (BG-12)), alemtuzumab (Lemtrada®)), or an anti-LINGO-1 antibody.

Combination with Other Tests

The methods of the invention can further include the step of monitoring the subject, e.g., for a change (e.g., an increase or decrease) in one or more of: levels of one or more MS biomarkers; the rate of appearance of new lesions, e.g., in an MRI scan; the appearance of new disease-related symptoms; a change in EDSS score; a change in quality of life; or any other parameter related to clinical outcome.

In one embodiment, the methods described herein further include one or more steps of: performing a neurological and/or neuropsychological evaluation, evaluating the subject's status on the Expanded Disability Status Scale (EDSS), or detecting the subject's lesion status (e.g., as assessed using an MRI).

The subject can be monitored in one or more of the following periods: prior to beginning of treatment; during the treatment; or after the treatment has been administered. Monitoring can be used to evaluate the need for further treatment with the same MS therapy, or for additional MS treatment. Generally, a decrease in one or more of the parameters described above is indicative of the improved condition of the subject.

In certain embodiment, responsive to a determination of the value of the composite parameter and/or monitoring, the method further includes one or more of:

(1) stratifying a patient population (e.g., assigning a subject, e.g., a patient, to a group or class);

(2) identifying or selecting the subject as likely or unlikely to respond to a treatment;

(3) selecting a treatment option, e.g., administering or not administering an MS therapy; or (4) prognosticating the time course of the disease in the subject (e.g., evaluating the likelihood of increased or decreased patient survival).

Systems

In another aspect, the invention features a system for evaluating a subject (e.g., a patient, a patient group or a patient population). The system includes at least one processor operatively connected to a memory, the at least one processor when executing is configured to:

determine or calculate a value of a composite parameter associated with the subject, wherein the processor is further configured to calculate the value of the composite parameter responsive to establishing an attention factor for the subject and a memory factor for the subject; and evaluate the subject, based on at least one value of the composite parameter established, e.g., prior to, during, or after the conclusion of, an MS therapy, or established responsive to administration of an MS therapy.

In a related aspect, the invention features a system for monitoring a subject (e.g., monitoring disease progression in the subject), having multiple sclerosis (MS), or at risk for developing MS, comprising:

at least one processor operatively connected to a memory, the at least one processor when executing is configured to:

establish a value of a composite parameter associated with the subject, prior to, during, and/or after an MS therapy, wherein the processor is further configured to establish the value of the composite parameter responsive to establishing an attention factor for the subject and a memory factor for the subject;

compare the value of the composite parameter from the subject to a reference value, (optionally) establish a reference value reflective of a severity of MS associated with the subject, and identify an indication of improved cognitive function in the subject in response to MS therapy, wherein identifying the indication of improved cognitive function includes detecting an increase in the value of the composite parameter, relative to the reference value; or identify an indication of decreased cognitive function in the subject in response to MS therapy, wherein identifying the indication of decreased cognitive function includes detecting a decrease in the value of the composite parameter, relative to the reference value.

In certain embodiments of the systems as described herein, the processor when executing is further configured to perform one or more of:

comparing the value of the composite parameter from the subject to a specified parameter, e.g., a reference value as described herein;

identifying the subject as being in need of an MS therapy;

recommending administration of an MS therapy;

determining or altering a dosing of the MS therapy;

determining or altering a schedule or a time course of the MS therapy; or recommending an alternative MS therapy.

In one embodiment of the systems as described herein, the processor when executing is further configured to establish the reference value with a higher value for a patient having relapse remitting multiple sclerosis (RRMS) when compared to a reference value for a patient with secondary progressive multiple sclerosis (SPMS).

In another embodiment, the processor when executing is further configured to identify an indication of improved cognitive function in the subject, wherein identifying the indication of improved cognitive function includes detecting an increase in the value of the composite parameter, relative to the reference value.

In yet another embodiment, the processor when executing is further configured to identify an indication of decreased cognitive function in the subject, wherein identifying the indication of decreased cognitive function includes detecting a decrease in the value of the composite parameter, relative to the reference value.

The reference value can be adjusted based at least in part on the timing of establishing a first composite value and at least one subsequent composite value.

In yet other embodiments of the system, the processor when executing is further configured to determine the value of the composite parameter based on evaluation of a plurality of attention and memory factors, e.g., one, two, three, four or more attention and memory factors.

In other embodiments of the system, the processor when executing is further configured to establish the memory factor from one or more verbal or visual memory factors.

In other embodiments of the system, the processor when executing is configured to determine the attention and memory factors, at least in part, from administering, or on the results from administration of, one, two, three, four or more of:

(i) an assessment of processes involved in learning and/or remembering visual information (e.g., Selective Reminding Test (SRT)), (ii) an assessment of visuospatial memory (e.g., Brief Visuospatial Memory Test (BVMT)), (iii) an assessment of complex scanning and/or visual tracking (e.g., Symbol Digit Modalities Test (SDMT), or (iv) an assessment of one or more of auditory information processing speed, flexibility or calculation ability (e.g., Paced Auditory Serial Addition Test (PASAT)). In one embodiment, the assessment includes a verbal instruction. In other embodiments, the assessment is supplied by an electronic means, e.g., a tablet; the electronic means can be used to capture the response.

In yet other embodiments of the system, the processor when executing is further configured to establish the reference value from one or more values obtained from testing of at least one of: a healthy subject or an average of healthy subjects; the subject at different time intervals (e.g., prior to, during, or after the MS therapy); a group of MS patients having the same or different disease progressions; the group of MS patients having the same or different disease progressions at different time intervals; a group of MS patients undergoing different MS treatments than the subject; or a group of MS patients undergoing a same MS treatment as the subject.

In other embodiments of the system, the processor when executing is further configured to compute an average value of one or more memory factors and one or more attention factors to determine the value of the composite parameter.

In other embodiments of the system, the processor when executing is further configured to compute an average value of the sum of an assessment of complex scanning and/or visual tracking and the average of at least two assessments of auditory information processing speed, flexibility or calculation ability.

In other embodiments of the system, the processor when executing is further configured to compute the value of the attention factor based on determining a value for the equation (SMDT+[PASAT 3+PASAT 2]/2))/2.

In other embodiments of the system, the one or more memory factors include a verbal memory factor, and wherein the processor when executing is further configured to compute the value of the verbal memory factor based on the average of the sum of at least two assessments of processes involved in learning and/or remembering visual information.

In other embodiments of the system, the one or more memory factors include a verbal memory factor, and wherein the processor when executing is further configured to compute the value of the verbal memory factor based on determining a value for the equation (SRT Total Learning+ SRT Delayed Recall)/2.

In other embodiments of the system, the one or more memory factors include a visual memory factor, and wherein the processor when executing is further configured to compute the value of the visual memory factor based on an average of at least two assessments of visuospatial memory.

In other embodiments of the system, the one or more memory factors include a visual memory factor, and wherein the processor when executing is further configured to compute the value of the visual memory factor based on determining a value for the equation (BVMT Total Recall+ BVMT Delayed Recall)/2.

In yet other embodiments of the system, the one or more memory factors include a visual memory factor and a verbal memory factor, wherein the processor when executing is further configured to compute the value of the one or more memory factors from the average of the value of the verbal memory factor and the visual memory factor.

In other embodiments of the system, the processor when executing is further configured to:
compute a reliability value for the composite parameter, and
evaluate the reliability value against a minimum threshold parameter including at least one of the threshold parameter set for at least 0.65, 0.69, 0.70, 0.75, 0.80, 0.85 or higher.

In other embodiments of the system, the processor when executing is further configured to perform one or more of the following responsive to a determination or comparison of the value of the composite parameter:
(1) stratify a patient population, wherein stratifying the patient population includes at least one of assigning a subject to a group or class having a common diagnostic characteristic;
(2) identify or select the subject as likely or unlikely to respond to a treatment;
(3) select a treatment option, including a determination to administer or not administer a preselected MS therapy; or
(4) generate a probabilistic model of the time course of the disease in the subject, including a determination of the likelihood of increased or decreased patient survival.

In other embodiments of the system, the processor when executing is further configured to:
store the value of the composite parameter, and
generate a report including analysis of the stored composite value, wherein the analysis is reflective of a status of the subject having MS.

In other embodiments of the system, the processor when executing is further configured to communicate information regarding a patient population including a plurality of the composite parameter corresponding to a plurality of subjects.

In other embodiments of the system, the processor when executing is further configured to communicate information regarding an evaluation of a subject or treatment to a report-receiving party or entity (e.g., a patient, a health care provider, a diagnostic provider, and/or a regulatory agency, e.g., the FDA).

In other embodiments of the system, the processor when executing is further configured to:
store a value of a composite parameter comprising an attention factor and memory factor, in a subject having multiple sclerosis (MS), or at risk for developing MS, prior to, during, and/or after the MS therapy; and
generate a correlation between the stored composite parameter and diagnosis of a status of the subject having MS;
communicate the correlation and the diagnosis to at least one of a health care provider, a diagnostic provider, and a regulatory agency.

In another aspect, the invention features system for evaluating and/or quantifying cognitive function, or evaluating disease progression, in a subject having MS, or at risk of developing MS. The system includes at least one processor operatively connected to a memory configured to:
establish a value of a composite parameter associated with the subject indicative of cognitive function, wherein the at least one processor is further configured to establish the value of the composite parameter responsive to establishing a first value for an attention and/or processing speed (PS) factor and a second value for a memory factor, wherein the at least one processor when executing is configured to:
compute an average value of scores from at least two assessments indicative of attention and/or processing speed to determine the first value, and
compute an average value of scores from at least one assessment of auditory/verbal learning and memory, and a score from at least one assessment of visual learning and memory to determine the second value;

compute the value of the composite parameter from a combination of the first and second values;

(optionally) compare the value of the composite parameter from the subject to a reference value, and identify an indication of improved cognitive function in the subject, wherein identifying the indication of improved cognitive function includes detecting an increase in the value of the composite parameter, relative to a reference value; or identify an indication of decreased cognitive function in the subject, wherein identifying the indication of decreased cognitive function includes detecting a decrease in the value of the composite parameter, relative to the reference value.

In another aspect, the invention features a computer implemented method for evaluating and/or quantifying cognitive function, or evaluating disease progression, in a subject having MS, or at risk for developing MS. The method comprises:

establishing, by a computer system, a value of a composite parameter associated with the subject indicative of cognitive function, wherein establishing the value of the composite parameter includes establishing a first value for an attention and/or processing speed (PS) factor and a second value for a memory factor, computing, by a computer system, an average value of scores from at least two assessments indicative of attention and/or processing speed to determine the first value, and computing, by a computer system, an average value of scores from at least one assessment of auditory/verbal learning and memory, and a score from at least one assessment of visual learning and memory to determine the second value;

computing, by a computer system, the value of the composite parameter from a combination of the first and second values;

(optionally) comparing, by the computer system, the value of the composite parameter from the subject to a reference value, and identifying, by the computer system, an indication of improved cognitive function in the subject, wherein identifying the indication of improved cognitive function includes detecting an increase in the value of the composite parameter, relative to a reference value; or identifying, by the computer system, an indication of decreased cognitive function in the subject, wherein identifying the indication of decreased cognitive function includes detecting a decrease in the value of the composite parameter, relative to the reference value.

Further embodiments of the system and computer-implemented methods include one or more of the following:

In certain embodiment, at least one processor of the system is configured to determine, or the method establishes, at least a portion of the first value by performing one or more of:

(i) compute an average value of the scores from at least one assessment of complex scanning and/or visual tracking, and the average value from at least one or two assessment(s) of processing speed, flexibility and/or calculation ability;

(ii) compute a function of a score based on a Symbol Digit Modalities Test (SMDT)) and a function of a score based on at least one or two Paced Auditory Serial Addition Test (PASAT); or (iii) compute the first value based on determining a value for the equation ((Symbol Digit Modalities Test (SDMT) score+(a first Paced Auditory Serial Addition Test ("PASAT") score (e.g., PASAT 3") and a second PASAT score (e.g., PASAT 2"))/2)/2.

In other embodiments, at least one processor of the system is configured to determine, or the method establishes, at least a portion of the second value by performing one or more of:

(i) compute an average value of the scores from at least one or two assessments indicative of verbal learning and delayed recall, and the average value of at least one or two assessments indicative of visual learning and delayed recall;

(ii) compute an average value of the scores from at least one or two components of a Selective Reminding Test (SRT) and at least one or two components of a Brief Visuospatial memory Test (BVMT); or (iii) compute the second value based on determining a value for the equation: [SRT learning score+SRT delay score+BVMT learning score and BVMT delay score]/4.

In certain embodiments, at least one processor of the system is further configured to compute, or the method establishes, a reliability value for the composite parameter, and evaluate the reliability value against a minimum threshold parameter including at least one of the threshold parameter set for at least 0.65, 0.69, 0.70, 0.75, 0.80, 0.85 or higher.

At least one processor of the system when executing can be further configured to, or the method includes a step to, weigh equally the first and the second values, or configured to weigh differentially (e.g., said first or second value being about 10%, 20%, 25%, 30%, 40%, 60%, 75% or more the value of the other value).

In other embodiments, the at least one processor of the system when executing is further configured to, or the method includes a step to, weigh equally or differentially (e.g., as described herein) the scores from the assessments used to obtain the second value.

In yet other embodiments, the at least one processor of the system when executing is further configured to, or the method includes a step to, weigh equally or differentially (e.g., as described herein) the scores from the assessments of verbal and visual memory. The system can be further configured to weigh equally or differentially the scores from the assessments of learning and delayed recall components.

In other embodiments, the at least one processor of the system when executing is further configured to, or the method includes a step to, weigh equally or differentially the scores from the at least one assessment of complex scanning and/or visual tracking, and the scores from the at least one or two assessment(s) of processing speed, flexibility and/or calculation ability.

In certain embodiments, the at least one processor of the system is configured to, or the method includes a step to, evaluate the composite parameter against a probabilistic model of a time course progression of disease effect on cognition for the subject, wherein the probabilistic model includes the reference value.

In other embodiments, the at least one processor of the system is configured to, or the method includes a step to, generate the probabilistic model of the time course progression of the disease effect on cognition for the subject including a time course of the reference value.

In one embodiment, the at least one processor of the system is configured to, or the method includes a step to, generate the probabilistic model from at least one or more of: a healthy subject; a group of healthy subjects; the subject prior to, during, or after the MS therapy; a group of MS patients having the same disease progressions; a group of MS patients having different disease progressions; a group of MS patients having the same or different disease progressions at different time intervals; a group of MS patients undergoing different MS treatments than the subject; or a group of MS patients undergoing a same MS treatment as the subject.

In another embodiment, the at least one processor of the system is configured to, or the method includes a step to, identify patients having similar MS disease progression from a model population.

In other embodiments, the at least one processor of the system is configured to, or the method includes a step to:

compute a SRT Total Learning value, SRT Delayed Recall value, BVMT Total Recall value, BVMT Delayed Recall value to establish a memory factor portion for the reference value;

compute a SDMT value, a first PASAT, a second PASAT value to establish an attention factor portion; and compute a combination of the memory factor portion and the attention factor portion to obtain the reference value.

In other embodiments, the at least one processor of the system when executing is further configured to, or the method includes a step to, perform one or more of:

comparing the value of the composite parameter from the subject to a reference value for a time parameter defined for a course of MS progression;
identifying the subject as being in need of an MS therapy;
recommending administration of an MS therapy;
determining or altering a dosing of the MS therapy;
determining or altering a schedule or a time course of the MS therapy; and
recommending an alternative MS therapy.

In other embodiments, the at least one processor of the system when executing is further configured to, or the method includes a step to:

capture a plurality of values of the composite parameter for the subject over time, and generate a model of the time course progression of the composite parameter, wherein the model is reflective of a disease state of the subject having MS.

Kits

In another aspect, the invention features kits for acquiring a value of the composite parameter for a subject, e.g., an MS patient. The kit can include means or tests for evaluating one, two, three, four or more attention and memory factors described herein. In certain embodiments, the kit includes one, two, three, four or more of:

(i) an assessment of processes involved in learning and/or remembering visual information (e.g., Selective Reminding Test (SRT)), (ii) an assessment of visuospatial memory (e.g., Brief Visual/spatial Memory Test (BVMT)), (iii) an assessment of complex scanning and/or visual tracking (e.g., Symbol Digit Modalities Test (SDMT), or (iv) an assessment of one or more of auditory information processing speed, flexibility or calculation ability (e.g., Paced Auditory Serial Addition Test (PASAT));

and means for determining the value of the composite parameter, e.g., a value of a composite parameter associated with the subject, prior to, during, and/or after an MS therapy.

Reports

The methods, systems, and/or kits described herein can further include providing or generating, and/or transmitting information, e.g., a report, containing data of the evaluation or treatment determined by the methods, and/or kits as described herein. In one embodiment, the value of the composite parameter is memorialized. The value or information can be transmitted to a report-receiving party or entity (e.g., a patient, a health care provider, a diagnostic provider, and/or a regulatory agency, e.g., the FDA), or otherwise submitting information about the methods and kits disclosed herein to another party. The method can relate to compliance with a regulatory requirement, e.g., a pre- or post approval requirement of a regulatory agency, e.g., the FDA. In one embodiment, the report-receiving party or entity can determine if a predetermined requirement or reference value is met by the data, and, optionally, a response from the report-receiving entity or party is received, e.g., by a physician, patient, diagnostic provider.

In other embodiments, a method for generating a report, includes acquiring a value of a composite parameter comprising an attention factor and memory factor, in a subject (e.g., a patient, a patient group or a patient population), having multiple sclerosis (MS), or at risk for developing MS, prior to, during, and/or after the MS therapy; and memorializing the value acquired.

In one aspect, the invention features a method for generating a report, comprising: acquiring a value of a composite parameter comprising an attention factor and memory factor, in a subject having multiple sclerosis (MS), or at risk for developing MS, prior to, during, and/or after the MS therapy; and memorializing the value in the report.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

BRIEF DESCRIPTION OF THE FIGURES

FIG. 7 is a schematic of general-purpose computer systems 604, 606, and 608 communicating over network 602.

DETAILED DESCRIPTION OF THE INVENTION

Figure 1:
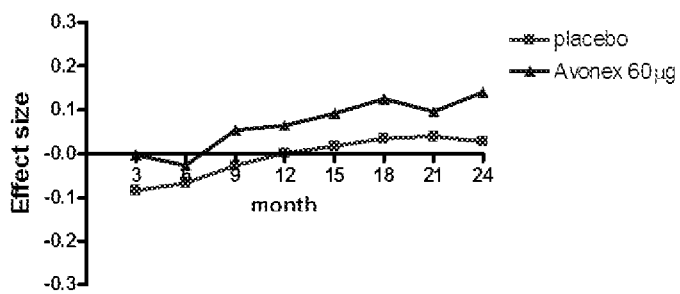
FIG. 1A is a line graph depicting the effect size of PASAT in SPMS subjects from the IMPACT trial.
FIG. 1B is a line graph depicting the effect size of PASAT in PPMS subjects from the OLYMPUS trial.
Figure 1:
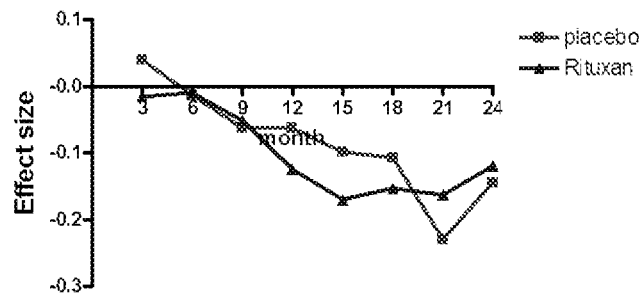

The present invention provides, at least in part, methods, systems and kits for the identification, assessment and/or treatment of a subject having a neurological disorder, e.g., multiple sclerosis (MS). In one embodiment, the methods, systems and kits include the step of detecting and/or quantifying a cognitive impairment in the subject (e.g., an MS patient), by obtaining a composite cognitive endpoint that includes a measure of processing speed and a measure of learning and memory (referred to herein as an "attention factor" and a "memory factor," respectively).

Composite cognitive endpoints offer several advantages over current methodologies, including, but not limited to, increased sensitivity, enhanced statistical power, smaller sampling size and enhanced simplicity. The invention can, therefore, be used, for example, for one or more of: (i) diagnosing, prognosing and/or evaluating, a subject (e.g., an MS patient); (ii) evaluating responsiveness to, or monitoring, a therapy (e.g., an MS therapy); (iii) identifying a patient as being stable, or showing an improvement or disease progression; (iv) to stratify a subject (e.g., an MS patient or patient population) as being a disease non-progressor or a disease progressor; and/or (v) more effectively monitoring, treating multiple sclerosis, or preventing worsening of disease and/or relapse.

Various aspects of the invention are described in further detail in the following subsections.

Definitions

As used herein, each of the following terms has the meaning associated with it in this section.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"Acquire" or "acquiring" as the terms are used herein, refer to obtaining possession of, determining, or evaluating, a value, e.g., a numerical value, by "directly acquiring" or "indirectly acquiring" the value. "Directly acquiring" means performing a process (e.g., performing a test, e.g., a cognitive test) to obtain the value. "Indirectly acquiring" refers to receiving the value from another party or source (e.g., a third party clinician or health professional that directly acquired the value).

A "composite parameter" as used herein in the context of cognitive endpoints refers to an integration of pre-selected measures of cognitive function (including, e.g., a measure of processing speed and a measure of learning and memory) into a consolidated index(es) or value(s). In the context of MS, the value of the composite parameter can be indicative of cognitive function in a domain including one or more of: information processing speed, information processing efficiency, visual memory, verbal memory (e.g., memory acquisition), executive function or perceptual processing. In certain embodiments, the composite parameter used is an average value of one or more memory factors and one or more attention factors.

Multiple sclerosis is "treated," "inhibited" or "reduced," if at least one symptom of the disease is reduced, alleviated, terminated, slowed, or prevented. As used herein, multiple sclerosis is also "treated," "inhibited," or "reduced," if recurrence or relapse of the disease is reduced, slowed, delayed, or prevented. Exemplary clinical symptoms of multiple sclerosis that can be used to aid in determining the disease status in a subject can include e.g., tingling, numbness, muscle weakness, loss of balance, blurred or double vision, slurred speech, sudden onset paralysis, lack of coordination, cognitive difficulties, fatigue, heat sensitivity, spasticity, dizziness, tremors, gait abnormalities, speech/swallowing difficulties, and extent of lesions assessed by imaging techniques, e.g., MRI. Clinical symptoms of MS are routinely classified and standardized, e.g., using an EDSS rating system. Typically, a decrease of one full step indicates an effective MS treatment (Kurtzke, Ann. Neurol. 36:573-79, 1994), while an increase of one full step will indicate the progression or worsening of the disease (e.g., exacerbation).

As used herein, the "Expanded Disability Status Scale" or "EDSS" is intended to have its customary meaning in the medical practice. EDSS is a rating system that is frequently used for classifying and standardizing MS. The accepted scores range from 0 (normal) to 10 (death due to MS). Typically patients having an EDSS score of about 6 will have moderate disability (e.g., walk with a cane), whereas patients having an EDSS score of about 7 or 8 will have severe disability (e.g., will require a wheelchair). More specifically, EDSS scores in the range of 1-3 refer to an MS patient who is fully ambulatory, but has some signs in one or more functional systems; EDSS scores in the range higher than 3 to 4.5 show moderate to relatively severe disability; an EDSS score of 5 to 5.5 refers to a disability impairing or precluding full daily activities; EDSS scores of 6 to 6.5 refer to an MS patient requiring intermittent to constant, or unilateral to bilateral constant assistance (cane, crutch or brace) to walk; EDSS scores of 7 to 7.5 means that the MS patient is unable to walk beyond five meters even with aid, and is essentially restricted to a wheelchair; EDSS scores of 8 to 8.5 refer to patients that are restricted to bed; and EDSS scores of 9 to 10 mean that the MS patient is confined to bed, and progressively is unable to communicate effectively or eat and swallow, until death due to MS.

"Responsiveness," to "respond" to treatment, and other forms of this verb, as used herein, refer to the reaction of a subject to treatment, e.g., an MS therapy (e.g., an MS therapy as described herein). As an example, a subject responds to treatment with the MS therapy, if at least one symptom of multiple sclerosis (e.g., cognitive (e.g., value of the composite parameter) or relapse rate) in the subject is improved, reduced or retarded by about 10%, 20%, 30%, 40%, 50%, 60%, 70%, 80%, 90% or more. For example, a value of at least 0.2, 0.3, 0.4, 0.5, 0.6, 0.7, 0.8, 0.9, 1.0, 1.1, 1.2, 1.3, 1.4, or 1.5 SD, greater than, or lower than, a specified parameter indicates that the subject has increased or decreased cognitive function, respectively, thus indicating that the subject is more or less responsive to the treatment, respectively. In another example, a subject responds to MS therapy, if at least one symptom of multiple sclerosis in the subject is reduced by about 5%, 10%, 20%, 30%, 40%, 50% or more as determined by any appropriate measure, e.g., Expanded Disability Status Scale (EDSS) or determining the extent of other symptoms such as relapse rate, muscle weakness, tingling, and numbness. In another example, a subject responds to MS therapy, if the subject experiences a life expectancy extended by about 5%, 10%, 20%, 30%, 40%, 50% or more beyond the life expectancy predicted if no treatment is administered. Several methods can be used to determine if a patient responds to a treatment including the cognitive (e.g., value of the composite parameter described herein) and/or EDSS criteria, as set forth above.

A "responder" or "non-progressor" refers to a subject, e.g., an MS patient, if in response to an MS therapy (e.g., an MS therapy described herein), at least one symptom of multiple sclerosis (e.g., cognitive impairment and/or physical) in the subject is reduced by about 5%, 10%, 20%, 30%, 40%, 50% or more as determined by any appropriate measure, e.g., a composite of cognitive test instruments, EDSS and/or determining the extent of other symptoms such as relapse rate, muscle weakness, tingling, and numbness. In one embodiment, a responder or non-progressor is defined as a subject with no confirmed relapses and no evidence of sustained disability progression (by EDSS) during the first three years of treatment (e.g., clinical remission).

A "non-responder" or "progressor" refers to a subject, e.g., an MS patient, if in response to an MS therapy (e.g., an MS therapy described herein), at least one symptom of multiple sclerosis (e.g., cognitive impairment and/or physical) in the subject is reduced by less than about 5%, as determined by any appropriate measure, e.g., a composite of cognitive test instruments, EDSS and/or determining the extent of other symptoms such as relapse rate, muscle weakness, tingling, and numbness. In one embodiment, a non-responder or progressor is defined as those subjects that have active disease on therapy including subjects with at least 3 relapses, development of a 6-month sustained progression in disability defined as a 1.0 point increase in EDSS score from baseline in subjects with a baseline score of $\leq 5.5$.

The cognitive composite score can be used to identify confirmed progressors and confirmed non-progressors. For this, the MS subject can take the test on at least 2 different occasions at least 1 month apart. Subject who have improvement by at least 0.25, 0.5 SD on the two occasions can be identified as a responder. A subject who does not have improvement of at least 0.25, 0.5 SD can be identified as a non-responder.

As used herein, "significant event" shall refer to an event in a patient's disease that is important as determined by one skilled in the art. Examples of significant events include, for example, without limitation, primary diagnosis, death, recurrence, remission, relapse of a patient's disease or the progression of a patient's disease from any one of the above noted stages to another. A significant event can be any important event used determine disease status using e.g., EDSS or other symptom criteria, as determined by one skilled in the art.

As used herein, "time course" shall refer to the amount of time between an initial event and a subsequent event. For example, with respect to a patient's disease, time course can relate to a patient's disease and can be measured by gauging significant events in the course of the disease, wherein the first event can be diagnosis and the subsequent event can be remission or relapse, for example.

Various aspects of the invention are described in further detail below. Additional definitions are set out throughout the specification.

Cognitive Test Instruments

Several cognitive test instruments can be used to determine the value of the composite parameter, as follows.

Symbol Digit Modalities Test (SDMT)

The SDMT is a test that evaluates processing speed and working memory in which the subject is given 90 seconds to pair specific numbers with given geometric figures based on a reference key. It is modeled after the Digit Symbol or Coding Tasks tests, which have been included in the Wechsler intelligence scales for many years (e.g., Wechsler et al. (1974) *Manual for the Wechsler Intelligence Scale for Children—Revised.* New York: Psychological Corporation; Wechsler et al. (1981) *WAIS-R Manual*. New York: Psychological Corporation). Recognizing the limitations some patients have with manual dexterity, Rao and colleagues modified the SDMT to include only an oral response (Rao et al. (1991) *Neurology* 41: 685-691). In this oral SDMT selected in the present invention, participants are presented with an 8.5×11 inch sheet that contains the numbers and symbols to be processed. The top row of stimuli includes nine symbols, each of which is paired with a single digit in the key. The remainder of the page has a pseudo-randomized sequence of these symbols, and the participant's task is to respond orally with the digit associated with each of the symbols as quickly as possible. The score is the total number of correct matches (out of 110) made by the subject within the 90 second time frame.

Good test-retest reliability ($r=0.93-0.97$, $p<0.001$) has been established in MS subjects (Benedict et al. (2006) *Journal of the International Neuropsychological Society* 12: 549-558; Benedict et al. (2008) *Multiple Sclerosis* 14: 940-946). Good discriminative validity for distinguishing between MS patients and normal controls ($d=1.0-1.5$, $p<0.001$) (see e.g., Deloire et al. (2005) *Journal of Neurology, Neurosurgery & Psychiatry* 76: 519-526; Benedict et al. (2006) *Journal of the International Neuropsychological Society* 12: 549-558; Houtchens et al. (2007) *Neurology* 69: 113-123; Strober et al. (2009) *Multiple Sclerosis* 15: 1077-1084; Parmenter et al. (2010) *J Int Neuropsychol Soc* 16: 6-16) and for distinguishing between RRMS and SPMS patients ($d=0.8$, $p<0.001$) (see Benedict et al. (2006) *Archives of Neurology* 63: 1301-1306) has also been confirmed. In addition, correlations between performance and brain MRI have also been documented (see e.g., Benedict et al. (2007) *Multiple Sclerosis* 13: 722-730; Houtchens et al. (2007) *Neurology* 69: 113-123; Tekok-Kilic et al. (2007) *Neuro Image* 36: 1294-1300).

Paced Serial Addition Test (PASAT)

First developed by Gronwall et al. to assess patients recovering from concussion, the PASAT requires patients to monitor a series of 61 audiotaped digits while adding each consecutive digit to the one immediately preceding it (Gronwall et al. (1977) *Perceptual and Motor Skills* 44: 367-373). The PASAT requires both rapid information processing and simultaneous allocation of attention to two tasks, as well as reasonably intact calculation ability. In its original format, the PASAT was administered at four inter-stimulus intervals (2.4 seconds, 2.0 seconds, 1.6 seconds, and 1.2 seconds). The number of inter-stimulus intervals and presentation rates were subsequently modified by Rao and colleagues for use with MS patients to 3.0 seconds and 2.0 seconds (Rao et al. (1991) A Manual for the Brief, Repeatable Battery of Neuropsychological Tests in Multiple Sclerosis: National Multiple Sclerosis Society; Rao et al. (1991) Neuropsychological Screening Battery for Multiple Sclerosis: National Multiple Sclerosis Society; Rao et al. (1991) *Neurology* 41: 685-691; Rao et al. (1991) *Neurology* 41: 692-696).

This latter version of the test was selected to be a component of the MS Functional Composite and the MACFIMS battery (Benedict et al. (2002) *Clinical Neuropsychologist* 16: 381-397). Test-retest reliability in MS populations ranges from $r=0.78$ to $0.93$ (Benedict et al. (2006) *Journal of the International Neuropsychological Society* 16: 228-237; Drake et al. (2010) *Multiple Sclerosis* 16: 228-237). Good discriminative validity for distinguishing between MS patients and normal controls ($d=0.5-0.7$, $p<0.001$ to $0.34$) (Deloire et al. (2005) *Journal of Neurology,*

Neurosurgery & Psychiatry 76: 519-526; Benedict et al. (2006) Journal of the International Neuropsychological Society 12: 549-558; Houtchens et al. (2007) Neurology 69: 113-123; Strober et al. (2009) Multiple Sclerosis 15: 1077-1084; Parmenter et al. (2010) J Int Neuropsychol Soc 16: 6-16; Drake et al. (2010) Multiple Sclerosis 16: 228-237) and for distinguishing between RRMS and SPMS patients (d=0.5, p<0.002) (Benedict et al. (2006) Archives of Neurology 63: 1301-1306) has been confirmed. The PASAT score of interest is the total number of correct responses at each presentation rate. Two alternate forms of the Rao version of the PASAT are available (PASAT 3" and PASAT 2") and were selected in the current invention. In the PASAT 3", the stimulus is presented every 3 seconds, where as in the PASAT 2", the stimulus is presented every 2 seconds.

Selective Reminding Test (SRT)

The SRT was first developed by Buschke et al. (see Buschke et al. (1974) Neurology 24: 1019-1025) who conducted research in the area of anterograde amnesia. Rather than ask patients to recall an entire word list on each successive learning trial, the experimenter only repeated words not recalled on each successive learning trial. Subsequently, several memory investigators developed normative data for the test, and alternate forms. Note, the original versions were based on a form of the test using 15 words and 12 learning trials. Such an administration is arduous and time consuming, and therefore there has been much interest in shorter forms of the SRT. The administration procedure widely used in MS research is a six-trial form developed by Rao et al. (see e.g., Rao et al. (1991) A Manual for the Brief, Repeatable Battery of Neuropsychological Tests in Multiple Sclerosis: National Multiple Sclerosis Society; Rao et al. (1991) Neuropsychological Screening Battery for Multiple Sclerosis: National Multiple Sclerosis Society; Rao et al. (1991) Neurology 41: 685-691; Rao et al. (1991) Neurology 41: 692-696). This six-trial format is utilized in the current invention. A number of different versions of SRT word lists exist. Hannay and Levin's word lists for adults, test forms 1 and 3, are utilized in the current invention (Hannay et al. (1985) J Clin Exp Neuropsychol. 7: 251-263). Discriminative validity of the SRT has been established in several studies, with SRT discriminating between MS subjects and normal controls d=0.6 to d=1.0 (see e.g., Rao et al. (1991) A Manual for the Brief, Repeatable Battery of Neuropsychological Tests in Multiple Sclerosis: National Multiple Sclerosis Society; Deloire et al. (2005) Journal of Neurology, Neurosurgery & Psychiatry 76: 519-526; Strober et al. (2009) Multiple Sclerosis 15: 1077-1084). It has also been shown that SRT findings correlate with ventricular enlargement as seen on brain MRI ($R^2$=0.14; p, 0.05) (Christodoulou et al. (2003) Neurology 60: 1793-1798).

Brief Visuospatial Memory Test-Revised (BVMT-R)

The BVMT-R is based on an initial effort to develop an equivalent alternate form visual memory test along the lines of the visual reproduction subtest from the Wechsler Memory Scale (Benedict et al. (1993) Neuropsychological Rehabilitation 3: 37-51; Benedict et al. (1995) Clinical Neuropsychologist 9: 11-16; Wechsler et al. (1987) Wechsler Memory Scale—Revised Manual. New York: Psychological Corporation). Initially, the BVMT included just a single exposure to a one-page presentation of six visual designs. The revised version includes three 10-second exposures to the stimulus (Benedict et al. (1997) Brief Visuospatial Memory Test—Revised: Professional Manual. Odessa, Fla.: Psychological Assessment Resources, Inc.; Benedict et al. (1996) Psychological Assessment 8: 145-153). After each exposure, the subject is asked to reproduce the matrix using a pencil on a blank sheet of paper. There are rigid scoring criteria for accuracy and location. After a 25 minute delay, the patient is asked to reproduce the information again without another exposure. Finally a yes/no recognition task is presented. The BVMT-R has excellent reproducibility, with test-retest reliability ranging from r=0.85 to r=0.91 (Benedict et al. (1996) Psychological Assessment 8: 145-153; Benedict et al. (2005) Journal of the International Neuropsychological Society 11: 727-736); as well as good discriminative validity between MS and normal control subjects (d=0.9, p<0.) (Strober et al. (2009) Multiple Sclerosis 15: 1077-1084; Parmenter et al. (2010) J Int Neuropsychol Soc 16: 6-16) and RRMS and SPMS patients (d=0.6, p<0.001) (Benedict et al. (2006) Archives of Neurology 63: 1301-1306). Predictive validity, in the form of correlation between BVMT-R performance and brain MRI findings, has also been established (Stankiewicz, J. M., B. I. Glanz, et al. (2011). "Brain MRI lesion load at 1.5T and 3T versus clinical status in multiple sclerosis." J Neuroimaging 21(2): e50-56). Further, there is extensive research showing that all 6 forms of the test are of equivalent difficulty. Variables of interest in the current invention are the Total Learning and Delayed Recall scores.

Multiple Sclerosis and Methods of Diagnosis

Multiple sclerosis (MS) is a central nervous system disease that is characterized by inflammation and loss of myelin sheaths.

Patients having MS can be identified by clinical criteria establishing a diagnosis of clinically definite MS as defined by Poser et al. (1983) Ann. Neurol. 13:227. Briefly, an individual with clinically definite MS has had two attacks and clinical evidence of either two lesions or clinical evidence of one lesion and paraclinical evidence of another, separate lesion. Definite MS may also be diagnosed by evidence of two attacks and oligoclonal bands of IgG in cerebrospinal fluid or by combination of an attack, clinical evidence of two lesions and oligoclonal band of IgG in cerebrospinal fluid. The McDonald criteria can also be used to diagnose MS. (McDonald et al. (2001) Recommended diagnostic criteria for Multiple sclerosis: guidelines from the International Panel on the Diagnosis of Multiple Sclerosis, Ann Neurol 50:121-127). The McDonald criteria include the use of MRI evidence of CNS impairment over time to be used in diagnosis of MS, in the absence of multiple clinical attacks. Effective treatment of multiple sclerosis may be evaluated in several different ways. The following parameters can be used to gauge effectiveness of treatment. Two exemplary criteria include: EDSS (extended disability status scale), and appearance of exacerbations on MRI (magnetic resonance imaging).

The EDSS is a means to grade clinical impairment due to MS (Kurtzke et al. (1983) Neurology 33:1444). Eight functional systems are evaluated for the type and severity of neurologic impairment. Briefly, prior to treatment, patients are evaluated for impairment in the following systems: pyramidal, cerebella, brainstem, sensory, bowel and bladder, visual, cerebral, and other. Follow-ups are conducted at defined intervals. The scale ranges from 0 (normal) to 10 (death due to MS). A decrease of one full step indicates an effective treatment (Kurtzke et al., (1994) Ann. Neurol. 36:573-79), while an increase of one full step will indicate the progression or worsening of disease (e.g., exacerbation). Typically patients having an EDSS score of about 6 will have moderate disability (e.g., walk with a cane), whereas patients having an EDSS score of about 7 or 8 will have severe disability (e.g., will require a wheelchair).

Exacerbations are defined as the appearance of a new symptom that is attributable to MS and accompanied by an appropriate new neurologic abnormality (IFNB MS Study Group, supra). In addition, the exacerbation must last at least 24 hours and be preceded by stability or improvement for at least 30 days. Briefly, patients are given a standard neurological examination by clinicians. Exacerbations are either mild, moderate, or severe according to changes in a Neurological Rating Scale (Sipe et al. (1984) *Neurology* 34:1368). An annual exacerbation rate and proportion of exacerbation-free patients are determined.

Therapy can be deemed to be effective using a clinical measure if there is a statistically significant difference in the rate or proportion of exacerbation-free or relapse-free patients between the treated group and the placebo group for either of these measurements. In addition, time to first exacerbation and exacerbation duration and severity may also be measured. A measure of effectiveness as therapy in this regard is a statistically significant difference in the time to first exacerbation or duration and severity in the treated group compared to control group. An exacerbation-free or relapse-free period of greater than one year, 18 months, or 20 months is particularly noteworthy. Clinical measurements include the relapse rate in one and two-year intervals, and a change in EDSS, including time to progression from baseline of 1.0 unit on the EDSS that persists for six months. On a Kaplan-Meier curve, a delay in sustained progression of disability shows efficacy. Other criteria include a change in area and volume of T2 images on MRI, and the number and volume of lesions determined by gadolinium enhanced images.

MRI can be used to measure active lesions using gadolinium-DTPA-enhanced imaging (McDonald et al., *Ann. Neurol.* 36:14, 1994) or the location and extent of lesions using T2-weighted techniques. Briefly, baseline MRIs are obtained. The same imaging plane and patient position are used for each subsequent study. Positioning and imaging sequences can be chosen to maximize lesion detection and facilitate lesion tracing. The same positioning and imaging sequences can be used on subsequent studies. The presence, location and extent of MS lesions can be determined by radiologists. Areas of lesions can be outlined and summed slice by slice for total lesion area. Three analyses may be done: evidence of new lesions, rate of appearance of active lesions, percentage change in lesion area (Paty et al., (1993) *Neurology* 43:665). Improvement due to therapy can be established by a statistically significant improvement in an individual patient compared to baseline or in a treated group versus a placebo group.

Exemplary symptoms associated with multiple sclerosis, which can be treated with the methods described herein or managed using symptom management therapies, include: optic neuritis, diplopia, nystagmus, ocular dysmetria, internuclear opthalmoplegia, movement and sound phosphenes, afferent pupillary defect, paresis, monoparesis, paraparesis, hemiparesis, quadraparesis, plegia, paraplegia, hemiplegia, tetraplegia, quadraplegia, spasticity, dysarthria, muscle atrophy, spasms, cramps, hypotonia, clonus, myoclonus, myokymia, restless leg syndrome, footdrop, dysfunctional reflexes, paraesthesia, anaesthesia, neuralgia, neuropathic and neurogenic pain, l'hermitte's, proprioceptive dysfunction, trigeminal neuralgia, ataxia, intention tremor, dysmetria, vestibular ataxia, vertigo, speech ataxia, dystonia, dysdiadochokinesia, frequent micturation, bladder spasticity, flaccid bladder, detrusor-sphincter dyssynergia, erectile dysfunction, anorgasmy, frigidity, constipation, fecal urgency, fecal incontinence, depression, cognitive dysfunction, dementia, mood swings, emotional lability, euphoria, bipolar syndrome, anxiety, aphasia, dysphasia, fatigue, uhthoffs symptom, gastroesophageal reflux, and sleeping disorders.

Each case of MS displays one of several patterns of presentation and subsequent course. Most commonly, MS first manifests itself as a series of attacks followed by complete or partial remissions as symptoms mysteriously lessen, only to return later after a period of stability. This is called relapsing-remitting MS (RRMS). Primary-progressive MS (PPMS) is characterized by a gradual clinical decline with no distinct remissions, although there may be temporary plateaus or minor relief from symptoms. Secondary-progressive MS (SPMS) begins with a relapsing-remitting course followed by a later primary-progressive course. Rarely, patients may have a progressive-relapsing (PRMS) course in which the disease takes a progressive path punctuated by acute attacks. PPMS, SPMS, and PRMS are sometimes lumped together and called chronic progressive MS.

A few patients experience malignant MS, defined as a swift and relentless decline resulting in significant disability or even death shortly after disease onset. This decline may be arrested or decelerated by determining the likelihood of the patient to respond to a therapy early in the therapeutic regime and switching the patient to an agent that they have the highest likelihood of responding to.

In addition to the physical symptoms described above, MS can also be associated with significant cognitive impairments. MS related cognitive symptoms can include, impairments in memory, information processing, attention and concentration, abstract conceptualization, visuospatial skills, verbal fluency, learning, executive functions, (e.g., high level processes, e.g., planning, prioritizing, and problem solving); difficulty reasoning or solving problems; decreased attention span; poor judgment; and memory loss.

The methods provided herein are particularly useful for identifying subjects that are more likely to respond to, or are in need of, an alternative therapy as described herein. In some embodiments, a composite parameter is measured prior to the initiation of a therapy, and based solely on the composite parameter or based on the composite parameter, alone or in combination with other factors (e.g., presence or absence or degree of physical symptoms associated with MS); an alternative therapy is recommended or administered. The methods provided herein are also particularly useful for identifying subjects that are not in need of an alternative therapy. In some embodiments, a composite parameter is measured prior to the initiation of a therapy, and based solely on the composite parameter, or based on the composite parameter in combination with other factors (e.g., presence/absence or degree of physical symptoms associated with MS).

The methods described herein can also be used to monitor a response to a therapy. Such methods are useful for detection of tolerance to a therapy, ineffectiveness of a therapy, or a positive response to a therapy. In some embodiments, a composite parameter is measured at least 2 weeks, at least 1 month, at least 3 months, at least 6 months, or at least 1 year after initiation of a therapy. In some embodiments, it is preferred that a composite parameter is measured less than 6 months after initiation of therapy to permit the skilled practitioner to switch the subject to a different therapeutic strategy. Thus, in some embodiments it is preferred that a composite parameter is measured within 1-6 months, 1-5 months, 1-4 months, 1-3 months, 1-2 months, 2-6 months, 3-6 months, 4-6 months, 5-6 months, 2-3 months, 3-4 months, or 4-5 months of initiation of therapy.

In some embodiments, the composite parameter is compared to a reference value or cut-off value. For example, a cut-off value can be determined that represents a particular therapy should be administered. In another example, a cut-off value can be determined that represents a non-responder status; any values falling below the cut-off value are likely to be non-responders to a current therapy.

In some embodiments, a change in the composite parameter is determined. In one embodiment, the change in the composite parameter is determined by comparing the composite parameter acquired for a subject with MS at two or more timepoints (e.g., at baseline and 3 months after initiation of therapy or 3 and 6 months after initiation of therapy).

The present invention also pertains to the field of predictive medicine in which diagnostic assays, pharmacogenomics, and monitoring clinical trials are used for predictive purposes to thereby treat an individual prophylactically. Accordingly, one aspect of the present invention relates to methods for determining a composite parameter, in order to determine whether an individual having multiple sclerosis or at risk of developing multiple sclerosis should be administered an alternative therapy.

In one aspect, the invention is drawn to a method for determining whether a subject is in need of a MS therapy. In another aspect, the method is drawn to selecting an MS therapy. In another aspect, the invention is drawn to a method of administering a MS therapy. In another aspect the, the invention is drawn to a method of altering dosing of a MS therapy. In another aspect, the invention is drawn to a method of altering a schedule or a time course of a MS therapy. In still another aspect, the invention is drawn to a method of administering an alternative MS therapy.

In certain embodiments, the method comprises acquiring a value of a composite parameter from a subject as described herein and determining whether the subject is in need of a MS therapy. In certain embodiments, the method comprises acquiring a value of a composite parameter from a subject as described herein and selecting; altering composition of; altering dosage of; or altering dosing schedule of; an MS therapy.

In some embodiments, the methods involve evaluation of a subject e.g., a patient, a patient group or a patient population, e.g., a patient who has been diagnosed with or is suspected of having multiple sclerosis, e.g., presents with symptoms of multiple sclerosis, to acquire a value of a composite parameter described herein.

In some embodiments, the results of the acquisition of the composite parameter and the interpretation thereof, are predictive of the patient's need for or response to treatment with an alternative therapy. According to the present invention, a composite parameter described herein, can be indicative that treatment with an alternative therapy should be recommended or administered.

In yet another embodiment, the composite parameter is assessed at pre-determined intervals, e.g., a first point in time and at least at a subsequent point in time. In one embodiment, a time course is measured by determining the time between significant events in the course of a patient's disease, wherein the measurement is predictive of whether a patient has a long time course. In another embodiment, the significant event is the progression from primary diagnosis to death. In another embodiment, the significant event is the progression from primary diagnosis to worsening disease. In another embodiment, the significant event is the progression from primary diagnosis to relapse. In another embodiment, the significant event is the progression from secondary MS to death. In another embodiment, the significant event is the progression from remission to relapse. In another embodiment, the significant event is the progression from relapse to death. In certain embodiments, the time course is measured with respect to one or more of overall survival rate, time to progression and/or using the EDSS or other assessment criteria.

The methods described herein can be used in any subject having multiple sclerosis including sub-types such as benign MS, quiescent relapsing-remitting MS, active relapsing-remitting MS, primary progressive MS, and secondary progressive MS. It is also contemplated, in other embodiments, that the methods can be used in subjects having MS-like symptoms, such as those having clinically isolated syndrome (CIS) or clinically defined MS (CDMS). Clinically isolated syndrome (CIS) refers to the detection of a single clinical episode of demyelination or other monophasic CNS inflammatory disorder (e.g., Spinal Cord Syndrome, Brainstem/Cerebellar Syndrome, and others described below). Frohman et al. (2003) Neurology 2003 61(5):602-11 report that, in subjects with CIS, three or more white matter lesions on a T2-weighted MRI scan (especially if one of these lesions is located in the periventricular region) is a very sensitive predictor (>80%) of the subsequent development of CDMS within the next 7 to 10 years. In a preferred embodiment, the methods described herein are used to assess expression of one or more biomarkers of Table 1 in a subject having RRMS.

In an aspect of the invention, the method is drawn to the evaluation of pharmaceutical agents for their effectiveness for treating MS. In some embodiments, the composite parameter is used as a measure of the effectiveness of a pharmaceutical agent for treating MS. In some embodiments, the change in the composite parameter assessed at pre-determined intervals, e.g., a first point in time and at least at a subsequent point in time, is used as a measure of the effectiveness of a pharmaceutical agent for treating MS.

MS Therapeutic Agents, Compositions and Administration

There are several medications presently used to modify the course of multiple sclerosis in patients. Such agents include, but are not limited to, Beta interferons (e.g., Avonex®, Rebif®, Betaseron®, Betaferon® etc.)), glatiramer (Copaxone®), natalizumab (Tysabri®), and mitoxantrone (Novantrone®).

IFNβ Agents (Beta Interferons)

One known therapy for MS includes treatment with interferon beta. Interferons (IFNs) are natural proteins produced by the cells of the immune systems of most animals in response to challenges by foreign agents such as viruses, bacteria, parasites and tumor cells. Interferons belong to the large class of glycoproteins known as cytokines. Interferon beta has 165 amino acids. Interferons alpha and beta are produced by many cell types, including T-cells and B-cells, macrophages, fibroblasts, endothelial cells, osteoblasts and others, and stimulate both macrophages and NK cells. Interferon gamma is involved in the regulation of immune and inflammatory responses. It is produced by activated T-cells and Th1 cells.

Several different types of interferon are now approved for use in humans. Interferon alpha (including forms interferon alpha-2a, interferon alpha-2b, and interferon alfacon-1) was approved by the United States Food and Drug Administration (FDA) as a treatment for Hepatitis C. There are two currently FDA-approved types of interferon beta. Interferon beta 1a (Avonex®) is identical to interferon beta found naturally in humans, and interferon beta 1b (Betaseron®) differs in certain ways from interferon beta 1a found naturally in humans, including that it contains a serine residue in place of a cysteine residue at position 17. Other uses of interferon beta have included treatment of AIDS, cutaneous T-cell lymphoma, Acute Hepatitis C (non-A, non-B), Kaposi's sarcoma, malignant melanoma, and metastatic renal cell carcinoma.

IFNβ agents can be administered to the subject by any method known in the art, including systemically (e.g., orally, parenterally, subcutaneously, intravenously, rectally, intramuscularly, intraperitoneally, intranasally, transdermally, or by inhalation or intracavitary installation). Typically, the IFNβ agents are administered subcutaneously, or intramuscularly.

IFNβ agents can be used to treat those subjects determined to be "responders" using the methods described herein. In one embodiment, the IFNβ agents are used as a monotherapy (i.e., as a single "disease modifying therapy") although the treatment regimen can further comprise the use of "symptom management therapies" such as antidepressants, analgesics, anti-tremor agents, etc. In one embodiment, the IFNβ agent is an IFNβ-1A agent (e.g., Avonex®, Rebif®). In another embodiment, the INFβ agent is an INFβ-1B agent (e.g., Betaseron®, Betaferon®).

Avonex®, an Interferon β-1a, is indicated for the treatment of patients with relapsing forms of MS that are determined to be responders using the methods described herein to slow the accumulation of physical disability and decrease the frequency of clinical exacerbations. Avonex® (Interferon beta-1a) is a 166 amino acid glycoprotein with a predicted molecular weight of approximately 22,500 daltons. It is produced by recombinant DNA technology using genetically engineered Chinese Hamster Ovary cells into which the human interferon beta gene has been introduced. The amino acid sequence of Avonex® is identical to that of natural human interferon beta. The recommended dosage of Avonex® (Interferon beta-1a) is 30 mcg injected intramuscularly once a week. Avonex® is commercially available as a 30 mcg lyophilized powder vial or as a 30 mcg prefilled syringe.

Interferon beta Ia (Avonex®) is identical to interferon beta found naturally in humans (AVONEX®, i.e., Interferon beta Ia (SwissProt Accession No. P01574 and gi:50593016).

In one embodiment, the interferon beta molecule includes the amino acid sequence of SEQ ID NO:1, or an amino acid sequence substantially homologous thereto (e.g., at least 70%, 80%, 90%, 95%, or more identical thereto).

Methods for Making Avonex® are Known in the Art.

Treatment of responders identified using the methods described herein further contemplates that compositions (e.g., IFN beta 1a molecules) having biological activity that is substantially similar to that of AVONEX® will permit successful treatment similar to treatment with AVONEX® when administered in a similar manner. Such other compositions include, e.g., other interferons and fragments, analogues, homologues, derivatives, and natural variants thereof with substantially similar biological activity. In one embodiment, the INFβ agent is modified to increase one or more pharmacokinetic properties. For example, the INFβ agent can be a modified form of interferon 1a to include a pegylated moiety. PEGylated forms of interferon beta 1a are described in, e.g., Baker, D. P. et al. (2006) *Bioconjug Chem* 17(1):179-88; Arduini, R M et al. (2004) *Protein Expr Purif* 34(2):229-42; Pepinsky, R B et al. (2001) *J. Pharmacol. Exp. Ther.* 297(3):1059-66; Baker, D. P. et al. (2010) *J Interferon Cytokine Res* 30(10):777-85 (all of which are incorporated herein by reference in their entirety, and describe a human interferon beta 1a modified at its N-terminal alpha amino acid to include a PEG moiety, e.g., a 20 kDa mPEG-O-2-methylpropionaldehyde moiety). Pegylated forms of IFN beta 1a can be administered by, e.g., injectable routes of administration (e.g., subcutaneously).

Rebif® is also an Interferon β-1a agent, while Betaseron® and Betaferon® are Interferon β-1b agents. Both Rebif® and Betaseron® are formulated for administration by subcutaneous injection.

Dosages of IFNβ agents to administer can be determined by one of skill in the art, and include clinically acceptable amounts to administer based on the specific interferon-beta agent used. For example, AVONEX® is typically administered at 30 microgram once a week via intramuscular injection. Other forms of interferon beta 1a, specifically REBIF®, is administered, for example, at 22 microgram three times a week or 44 micrograms once a week, via subcutaneous injection. Interferon beta-1A can be administered, e.g., intramuscularly, in an amount of between 10 and 50 µg. For example, AVONEX® can be administered every five to ten days, e.g., once a week, while Rebif® can be administered three times a week.

Non-IFNβ Agents

In subjects determined to be non-responders using the methods described herein, a skilled physician can select a therapy that includes a non-IFNβ agent, e.g., glatiramer (Copaxone®), natalizumab (Tysabri®, Antegren®), mitoxantrone (Novantrone®), dimethyl fumarate (BG-12®), a repatative agent; an anti-LINGO antibody, an inhibitor of a dihydroorotate dehydrogenase (e.g., teriflunomide), among others.

Steroids, e.g., corticosteroid, and ACTH agents can be used to treat acute relapses in relapsing-remitting MS or secondary progressive MS. Such agents include, but are not limited to, Depo-Medrol®, Solu-Medrol®, Deltasone®, Delta-Cortef®, Medrol®, Decadron®, and Acthar®.

Natalizumab (Tysabri)

Natalizumab inhibits the migration of leukocytes from the blood to the central nervous system. Natalizumab binds to VLA-4 (also called α4β1) on the surface of activated T-cells and other mononuclear leukocytes. It can disrupt adhesion between the T-cell and endothelial cells, and thus prevent migration of mononuclear leukocytes across the endothelium and into the parenchyma. As a result, the levels of pro-inflammatory cytokines can also be reduced. Natalizumab can decrease the number of brain lesions and clinical relapses in patients with relapse remitting multiple sclerosis and relapsing secondary-progressive multiple sclerosis.

Natalizumab and related VLA-4 binding antibodies are described, e.g., in U.S. Pat. No. 5,840,299. Monoclonal antibodies 21.6 and HP1/2 are exemplary murine monoclonal antibodies that bind VLA-4. Natalizumab is a humanized version of murine monoclonal antibody 21.6 (see, e.g., U.S. Pat. No. 5,840,299). A humanized version of HP 1/2 has also been described (see, e.g., U.S. Pat. No. 6,602,503). Several additional VLA-4 binding monoclonal antibodies, such as HP2/1, HP2/4, L25 and P4C2, are described, e.g., in U.S. Pat. No. 6,602,503; Sanchez-Madrid et al, (1986) *Eur. J. Immunol* 16:1343-1349; Hemler et al, (1987) *J Biol. Chem.* 2:11478-11485; Issekutz et al. (1991) *J Immunol* 147: 109 (TA-2 mab); Pulido et al. (1991) *J Biol. Chem.* 266: 10241-10245; and U.S. Pat. No. 5,888,507).

BG-12® (Dimethyl Fumarate)

BG-12® (dimethyl fumarate) is a fumaric acid ester. BG-12 is thought to decrease leukocyte passage through the blood brain barrier and exert neuroprotective effects by the activation of antioxidative pathways, specifically through activation of the Nrf-2 pathway (Lee et al. (2008) *Int MS Journal* 15: 12-18). Research also suggests that BG-12® has the potential to reduce the activity and impact of inflammatory cells on the CNS and induce direct cytoprotective responses in CNS cells. These effects may enhance the CNS cells' ability to mitigate the toxic inflammatory and oxidative stress that plays a role in MS pathophysiology.

Copaxone® (Glatiramer Acetate)

Copaxone® (glatiramer acetate) consists of the acetate salts of synthetic polypeptides, specifically the four naturally occurring amino acids: L-glutamic acid, L-alanine, L-tyrosine, and L-lysine (Bornstein et al. (1987) *N Engl J Med.* 317: 408-414). Copaxone® exhibits structural similarity to myelin basic protein and is thought to function as an immune modulator by shifting the T helper cell type 1 response towards a T helper cell type 2 response (Duda et al. (2000) *J Clin Invest* 105: 967-976; Nicholas et al. (2011) *Drug Design, Development, and Therapy* 5: 255-274).

Symptom Management

Treatment of a subject with a disease modifying IFNβ agent or non-IFNβ agent can be combined with one or more of the following therapies often used in symptom management of subjects having MS: Imuran® (azathioprine), Cytoxan® (cyclophosphamide), Neosar® (cyclophosphamide), Sandimmune® (cyclosporine), methotrexate, Leustatin® (cladribine), Tegretol® (carbamazepine), Epitol® (carbamazepine), Atretol® (carbamazepine), Carbatrol® (carbamazepine), Neurontin® (gabapentin), Topamax® (topiramate), Zonegran® (zonisamide), Dilantin® (phenytoin), Norpramin® (desipramine), Elavil® (amitriptyline), Tofranil® (imipramine), Imavate® (imipramine), Janimine® (imipramine), Sinequan® (doxepine), Adapin® (doxepine), Triadapin® (doxepine), Zonalon® (doxepine), Vivactil® (protriptyline), Marinol® (synthetic cannabinoids), Trental® (pentoxifylline), Neurofen® (ibuprofen), aspirin, acetaminophen, Atarax® (hydroxyzine), Prozac® (fluoxetine), Zoloft® (sertraline), Lustral® (sertraline), Effexor XR® (venlafaxine), Celexa® (citalopram), Paxil®, Seroxat®, Desyrel® (trazodone), Trialodine® (trazodone), Pamelor® (nortriptyline), Aventyl® (imipramine), Prothiaden® (dothiepin), Gamanil® (lofepramine), Parnate® (tranylcypromine), Manerix® (moclobemide), Aurorix® (moclobemide), Wellbutrin SR® (bupropion), Amfebutamone® (bupropion), Serzone® (nefazodone), Remeron® (mirtazapine), Ambien® (zolpidem), Xanax® (alprazolam), Restoril® (temazepam), Valium® (diazepam), BuSpar® (buspirone), Symmetrel® (amantadine), Cylert® (pemoline), Provigil® (modafinil), Ditropan XL® (oxybutynin), DDAVP® (desmopressin, vasopressin), Detrol® (tolterodine), Urecholine® (bethane), Dibenzyline® (phenoxybenzamine), Hytrin® (terazosin), Pro-Banthine® (propantheline), Urispas® (hyoscyamine), Cystopas® (hyoscyamine), Lioresal® (baclofen), Hiprex® (methenamine), Mandelamine® (metheneamine), Macrodantin® (nitrofurantoin), Pyridium® (phenazopyridine), Cipro® (ciprofloxacin), Dulcolax® (bisacodyl), Bisacolax® (bisacodyl), Sani-Supp® (glycerin), Metamucil® (psyllium hydrophilic mucilloid), Fleet Enema® (sodium phosphate), Colace® (docusate), Therevac Plus®, Klonopin® (clonazepam), Rivotril® (clonazepam), Dantrium® (dantrolen sodium), Catapres® (clonidine), Botox® (botulinum toxin), Neurobloc® (botulinum toxin), Zanaflex® (tizanidine), Sirdalud® (tizanidine), Mysoline® (primidone), Diamox® (acetozolamide), Sinemet® (levodopa, carbidopa), Laniazid® (isoniazid), Nydrazid® (isoniazid), Antivert® (meclizine), Bonamine® (meclizine), Dramamine® (dimenhydrinate), Compazine® (prochlorperazine), Transderm® (scopolamine), Benadryl® (diphenhydramine), Antegren® (natalizumab), Campath-1H® (alemtuzumab), Fampridine® (4-aminopyridine), Gammagard® (IV immunoglobulin), Gammar-IV® (IV immunoglobulin), Gamimune N® (IV immunoglobulin), Iveegam® (IV immunoglobulin), Panglobulin® (IV immunoglobulin), Sandoglobulin® (IV immunoglobulin), Venoblogulin® (IV immunoglobulin), pregabalin, ziconotide, and AnergiX-MS®.

In other embodiments, the method further includes the use of one or more therapies for management of cognitive and/or memory impairment. Examples of such therapies include, but are not limited to, agents that increase the level of neurotransmitters in the brain, NMDA receptor agents, and CNS stimulants (e.g., dextro or levo amphetamines).

A subject identified as a non-responder can be treated with one or more agents described herein to manage symptoms.

Therapeutic Methods

"Treat," "treatment," and other forms of this word refer to the administration of a therapy (e.g., an MS therapy), alone or in combination with one or more symptom management agents, to a subject, e.g., an MS patient, to impede progression of multiple sclerosis, to induce remission, to extend the expected survival time of the subject and or reduce the need for medical interventions (e.g., hospitalizations). In those subjects, treatment can include, but is not limited to, inhibiting or reducing one or more symptoms such as numbness, tingling, muscle weakness; reducing relapse rate, reducing size or number of sclerotic lesions; inhibiting or retarding the development of new lesions; prolonging survival, or prolonging progression-free survival, and/or enhanced quality of life.

As used herein, unless otherwise specified, the terms "prevent," "preventing" and "prevention" contemplate an action that occurs before a subject begins to suffer from the a multiple sclerosis relapse and/or which inhibits or reduces the severity of the disease.

As used herein, and unless otherwise specified, the terms "manage," "managing" and "management" encompass preventing the progression of disease (e.g., MS) symptoms in a patient who has already suffered from the disease, and/or lengthening the time that a patient who has suffered from the disease remains in remission. The terms encompass modulating the threshold, development and/or duration of MS, or changing the way that a patient responds to the disease.

As used herein, and unless otherwise specified, a "therapeutically effective amount" of a compound is an amount sufficient to provide a therapeutic benefit in the treatment or management of multiple sclerosis, or to delay or minimize one or more symptoms associated with the disease (e.g., MS). A therapeutically effective amount of a compound means an amount of therapeutic agent, alone or in combination with other therapeutic agents, which provides a therapeutic benefit in the treatment or management of MS. The term "therapeutically effective amount" can encompass an amount that improves overall therapy, reduces or avoids symptoms or causes of the disease, or enhances the therapeutic efficacy of another therapeutic agent.

As used herein, and unless otherwise specified, a "prophylactically effective amount" of a compound is an amount sufficient to prevent relapse of MS, or one or more symptoms associated with the disease, or prevent its recurrence. A prophylactically effective amount of a compound means an amount of the compound, alone or in combination with other therapeutic agents, which provides a prophylactic benefit in the prevention of MS relapse. The term "prophylactically effective amount" can encompass an amount that improves overall prophylaxis or enhances the prophylactic efficacy of another prophylactic agent.

As used herein, the term "patient" or "subject" refers to an animal, typically a human (i.e., a male or female of any age group, e.g., a pediatric patient (e.g., infant, child, adolescent) or adult patient (e.g., young adult, middle-aged adult or senior adult) or other mammal, such as a primate (e.g., cynomolgus monkey, rhesus monkey); commercially relevant mammals such as cattle, pigs, horses, sheep, goats, cats, and/or dogs; and/or birds, including commercially relevant birds such as chickens, ducks, geese, and/or turkeys, that will be or has been the object of treatment, observation, and/or experiment. When the term is used in conjunction with administration of a compound or drug, then the patient has been the object of treatment, observation, and/or administration of the compound or drug.

The methods described herein permit one of skill in the art to identify a monotherapy that an MS patient is most likely to respond to, thus eliminating the need for administration of multiple therapies to the patient to ensure that a therapeutic effect is observed. However, in one embodiment, combination treatment of an individual with MS is contemplated.

It will be appreciated that the MS therapies, as described above and herein, can be administered in combination with one or more additional therapies to treat and/or reduce the symptoms of MS described herein, particularly to treat patients with moderate to severe disability (e.g., EDSS score of 5.5 or higher). The pharmaceutical compositions can be administered concurrently with, prior to, or subsequent to, one or more other additional therapies or therapeutic agents. In general, each agent will be administered at a dose and/or on a time schedule determined for that agent. In will further be appreciated that the additional therapeutic agent utilized in this combination can be administered together in a single composition or administered separately in different compositions. The particular combination to employ in a regimen will take into account compatibility of the pharmaceutical composition with the additional therapeutically active agent and/or the desired therapeutic effect to be achieved. In general, it is expected that additional therapeutic agents utilized in combination be utilized at levels that do not exceed the levels at which they are utilized individually. In some embodiments, the levels utilized in combination will be lower than those utilized individually.

Systems and Computer Environment

In another aspect, the invention features a system for evaluating a subject (e.g., a patient, a patient group or a patient population). The system includes at least one processor operatively connected to a memory, the at least one processor when executing is configured to determine or calculate a value of a composite parameter associated with the subject, wherein the processor is further configured to calculate the value of the composite parameter responsive to establishing an attention factor for the subject and a memory factor for the subject; and evaluate the subject, based on at least one value of the composite parameter established, e.g., prior to, during, or after the conclusion of, an MS therapy, or established responsive to administration of an MS therapy.

Figure 3:
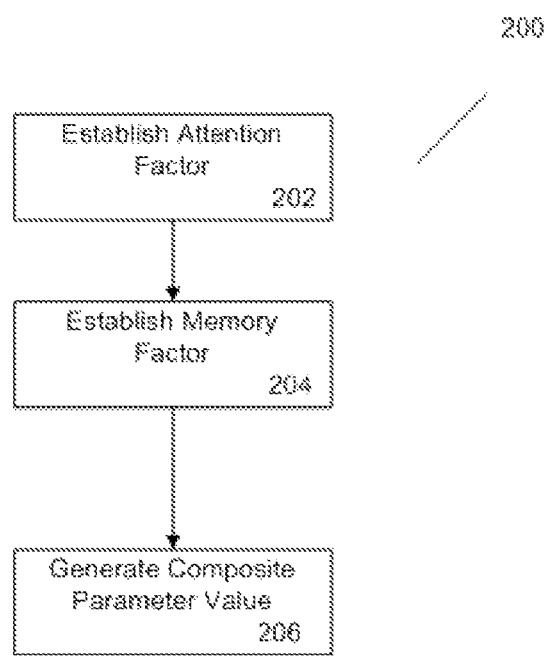
FIG. 3 illustrates an example process 200 for determining a composite parameter value for a subject, which can be executed on a computer system according to some embodiments.

According to some embodiments, users (e.g., physicians, researchers, clinicians, patients, and other medical personnel) can interact with computer systems especially configured to monitor, manage, diagnose, prognose, and/or facilitate treatment of subjects having MS or subjects at risk for developing MS. FIG. 3 illustrates an example process 200 for determining a composite parameter value for a subject, which can be executed on a computer system according to some embodiments. Process 200 begins at 202 by establishing an attention factor for the subject being evaluated. In some examples, the attention factor or a value for an attention factor can be input by a user based on results returned from external testing or captured from information on a subject's medical history. In some further examples, a computer system on which process 200 is executed can be configured to execute attention testing for a subject. In some embodiments, attention testing can be delivered through a user interface of a computer system. The computer system can include a plurality of sensors configured to determine and evaluate responsiveness of a subject to test stimuli. The results of the testing can be used to generate one or more values for an attention factor. The attention factor can be established at 202 by accessing and/or receiving any generated value for any attention factor.

In some embodiments, one or more values for the attention factor can be determined from the results of testing performed on a subject or by the subject. For example, one or more values for one or more attention factors can be computed as the result of an assessment of complex scanning and/or visual tracking (e.g., Symbol Digit Modalities Test (SDMT)) which in some embodiments can be configured to return as a portion of its results a test score, or as a result of an assessment of one or more of auditory information processing speed, flexibility or calculation ability (e.g., Paced Auditory Serial Addition Test (PASAT)) which in some embodiments can be configured to return as a portion of its results a test score. A value for an attention factor can be generated as the result of testing at 202 from any returned test score. One should appreciate that other processes for testing and scoring attention of a subject can be employed according to other embodiments. Further, other processes for testing and scoring can be used to generate one or more values for one or more attention factors.

Process 200 continues at 204 with establishing a value for a memory factor for the subject being evaluated. In some examples, the memory factor can be input by a user based on external testing. In some further examples, a computer system on which process 200 is executed can be configured to execute a plurality of memory based tests for a subject. In some embodiments, memory testing can be delivered through a user interface of a computer system. The results of the memory testing can be used to generate a value for a memory factor at 204. The value for the memory factor can also be established at 204 by accessing and/or receiving the determined value for the memory factor.

In some embodiments, one or more values for a memory factor can be determined from the results of testing performed on a subject or by the subject. For example, a value for a memory factor can be computed at 204 as the result of an assessment of processes involved in learning and/or remembering visual information (e.g., Selective Reminding Test (SRT)) which in some embodiments can be configured to return as a portion of its results a test score, or from an assessment of visuospatial memory (e.g., Brief Visuospatial Memory Test (BVMT)) which in some embodiments can be configured to return as a portion of its results a test score. One should appreciate that other processes for testing and scoring memory of a subject can be employed according to other embodiments to generate one or more values for one or more memory factors.

Process 200 continues at 206 where a composite parameter is generated from the one or more values for the one or more attention factors and the one or more values for the one or more memory factors. According to one embodiment, process 200 can be executed to calculate the composite parameter based on a calculation of the equation: (((SDMT+(PASAT 2 and PASAT 3)/2)/2+((SRT Total Learning value+

SRT Delayed Recall value)/2+(BVMT Total Recall value+ BVMT Delayed Recall value)/2)/2)/2. The value of the composite parameter reflects improvements in the accuracy of an assessment of a subject's mental acuity that can be used in conjunction with detailed analysis of physical health to define any one of progression of MS in the subject, likelihood of developing MS by the subject, treatment options, treatment efficacy, indications for changing treatment, among other options.

Figure 4:
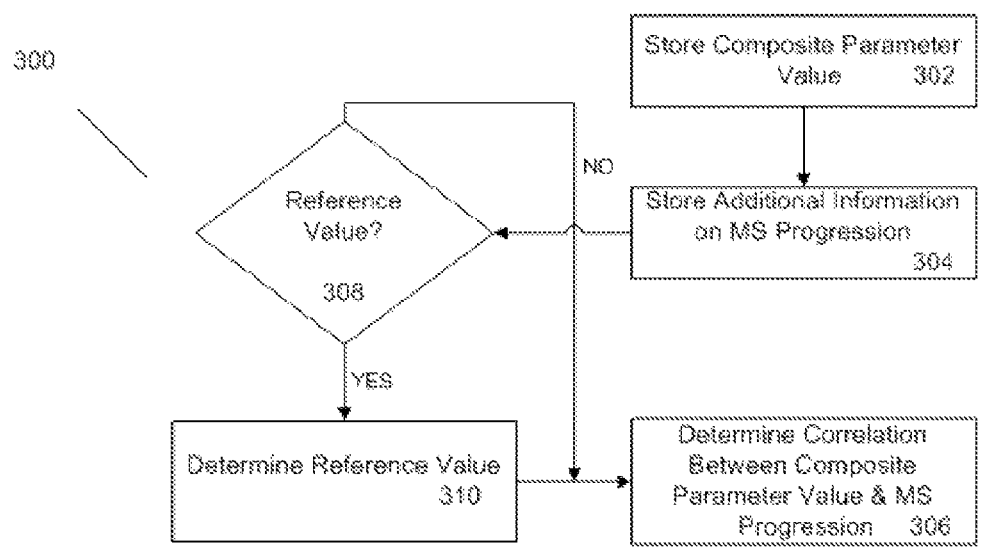
FIG. 4 illustrates an example process 300 that can be executed on a computer system for defining correlations between a composite parameter value and progression of MS or MS symptoms in a subject.

For example, FIG. 4, illustrates an example process 300 that can be executed on a computer system for defining correlations between a composite parameter value and progression of MS or MS symptoms in a subject. Process 300 begins at 302 with storing a value of a composite parameter. Step 302 can be executed repeatedly over time to establish a history for one or more subjects. The one or more subjects can include healthy patients (e.g., patients showing no MS symptoms or patients not expected to develop MS) as well as patients who may develop MS, and patients diagnosed with MS. At 304, additional information associated with MS progression for a respective subject, including, for example, a health condition of the respective subject, can also be stored at 304 for any execution of 302.

In some embodiments, the values obtained in 302 can be used to define a reference value 308 YES. The reference value can be used to define a baseline level for mental acuity. At 310, a reference value can be determined and optionally stored for later use. In some embodiments, comparisons can be made between the reference value and composite parameter values to determine a progression of MS, a likelihood of developing MS, efficacy of treatment for MS, to identify a need to change MS treatment, among other options. If a reference value is not presently being generated 308 NO or a reference value has been determined 310, process 300 continues at 306, where any correlation between the stored composite parameter values and MS progression can be determined. For example, composite parameter values for a first subject can be evaluated against subjects having a same or similar MS diagnosis. The progression of the first subject's MS can be used to predict the progression of MS in other subjects. The evaluation can also be used to identify a need for different or more aggressive treatment, for example, based on a prediction of worsening symptoms or outcome. In some embodiments, stored values for a plurality of subjects can be stored over time. The stored values can be used by the system to generate probabilistic models associated with the progression of MS and effect on cognition measured by the stored composite parameters. Additional subjects can be evaluated by the system against the models (e.g., at 310) to identify deviations from expected composite parameters defined by the models and/or the expected progression of MS for an evaluated subject.

Further, in some embodiments reference values determined at 310 can be included in the evaluation, and deviations from the reference values can be used to evaluate progression of a subject's MS. For example, reference values can be taken and/or determined over time, e.g., at a first and subsequent time point. Reference values determined over time can reflect an expected change in mental acuity based, for example, on progression of MS in a reference patient or an average progression determined from a group of patients. In one embodiments, deviations from the expected change (e.g., a higher composite parameter value than a reference score indicates improvement in the progression of the subject's MS even, for example, where the subject's mental acuity decreases over time (which can be reflected in analysis of the composite parameter values alone), and a composite parameter score lower than the time based reference indicates a worsening in the progression of the subject's MS) can be used to confirm an treatment in progress, identify need for a change in treatment, identify a need for a change in a time schedule of a treatment, etc. For example, the reference values determined over time can be used to evaluate subject over the course of a treatment, over the progression of MS for the subject, etc.

Various embodiments according to the present invention may be implemented on one or more specially programmed computer systems. These computer systems may be, for example, general-purpose computers such as those based on Intel PENTIUM-type processor, Motorola PowerPC, AMD Athlon or Turion, Sun UltraSPARC, Hewlett-Packard PA-RISC processors, or any other type of processor, including multi-core processors. It should be appreciated that one or more of any type computer system may be used to perform a method of evaluating a subject having multiple sclerosis (MS), or at risk of developing MS according to various embodiments of the invention. Further, the system may be located on a single computer or may be distributed among a plurality of computers attached by a communications network.

A general-purpose computer system according to one embodiment of the invention is specially configured to perform any of the described functions, including but not limited to, acquiring a value of a composite parameter from a subject, said composite parameter comprising an attention factor and a memory factor, identifying a subject as being in need of an MS therapy, administering a MS therapy, monitoring administration of an MS therapy, altering a dosing of the MS therapy, altering a schedule or a time course of a MS therapy, administering an alternative MS therapy, etc. Additional functions include, for example, comparing a value of the composite parameter from the subject to a reference value, performing one or more of: identifying the subject as being in need of an MS therapy, administering an MS therapy, altering a dosing of an MS therapy, altering a schedule or a time course of an MS therapy, or selecting an alternative MS therapy responsive to a determination of the value of the composite parameter.

It should be appreciated that the system may perform other functions, including identifying an increase in the value of the composite parameter relative to the reference value as indicative of improved cognitive function in the subject in response to MS therapy, determining a value of the composite parameter that differs according to the severity of MS, wherein an increase in the value of the composite parameter relative to the reference value, is indicative of improved cognitive function in the subject, identifying trends in the value of the composite parameter based at least in part on the type of MS, for example, in a patient having relapse remitting multiple sclerosis (RRMS) identifying patients having a lower composite parameter value compared to a patient with secondary progressive multiple sclerosis (SPMS), wherein a decrease in the value of the composite parameter, relative to a reference value, is indicative of decreased cognitive function in a subject, evaluating one, two, three, four or more attention and memory factors to determine a composite parameter, wherein, for example, the memory factor is chosen from one or more verbal or visual memory factors.

The functions, operations, and/or algorithms described herein can also be encoded as software executing on hardware that together define a processing component, that can further define one or more portions of a specially configured general purpose computer, that reside on an individual specially configured general purpose computer, and/or reside on multiple specially configured general purpose computers.

Figure 5:
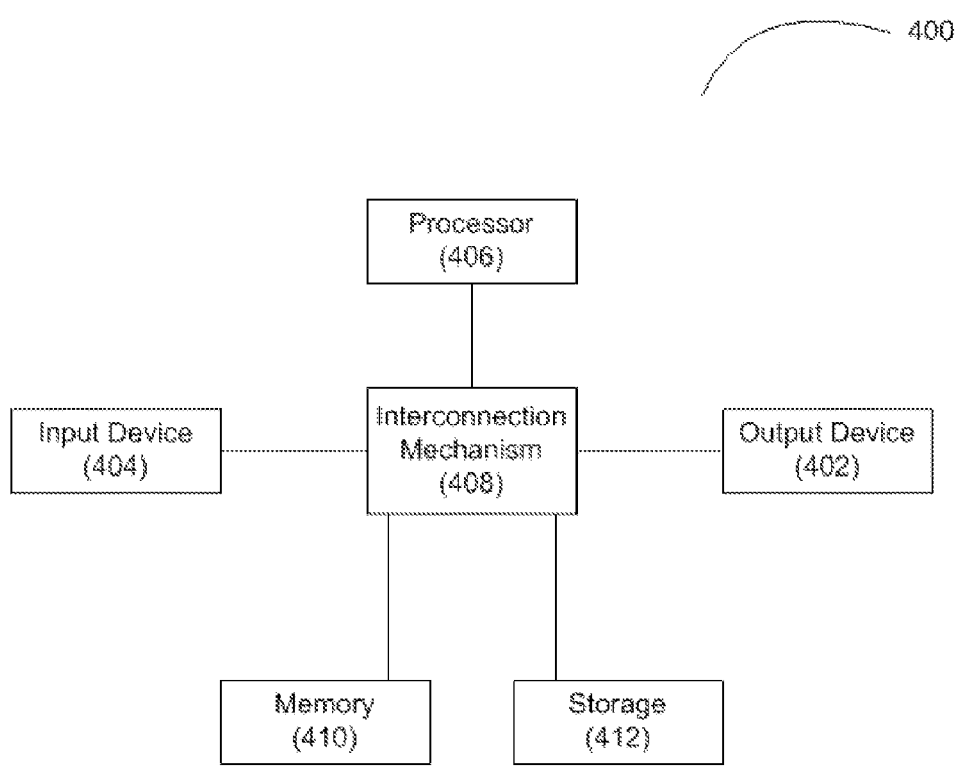
FIG. 5 shows an example block diagram of a general-purpose computer system 400 which can be especially configured to practice various aspects of the invention discussed herein.

FIG. 5 shows an example block diagram of a general-purpose computer system 400 which can be especially configured to practice various aspects of the invention discussed herein. For example, various aspects of the invention can be implemented as specialized software executing in one or more computer systems including general-purpose computer systems 604, 606, and 608 communicating over network 602 shown in FIG. 7. Computer system 400 may include a processor 406 connected to one or more memory devices 410, such as a disk drive, memory, or other device for storing data. Memory 410 is typically used for storing programs and data during operation of the computer system 400. Components of computer system 400 can be coupled by an interconnection mechanism 408, which may include one or more busses (e.g., between components that are integrated within a same machine) and/or a network (e.g., between components that reside on separate discrete machines). The interconnection mechanism 408 enables communications (e.g., data, instructions) to be exchanged between system components of system 400.

Computer system 400 may also include one or more input/output (I/O) devices 402-204, for example, a keyboard, mouse, trackball, microphone, touch screen, a printing device, display screen, speaker, etc. Storage 412, typically includes a computer readable and writeable nonvolatile recording medium in which instructions are stored that define a program to be executed by the processor or information stored on or in the medium to be processed by the program.

Figure 6:
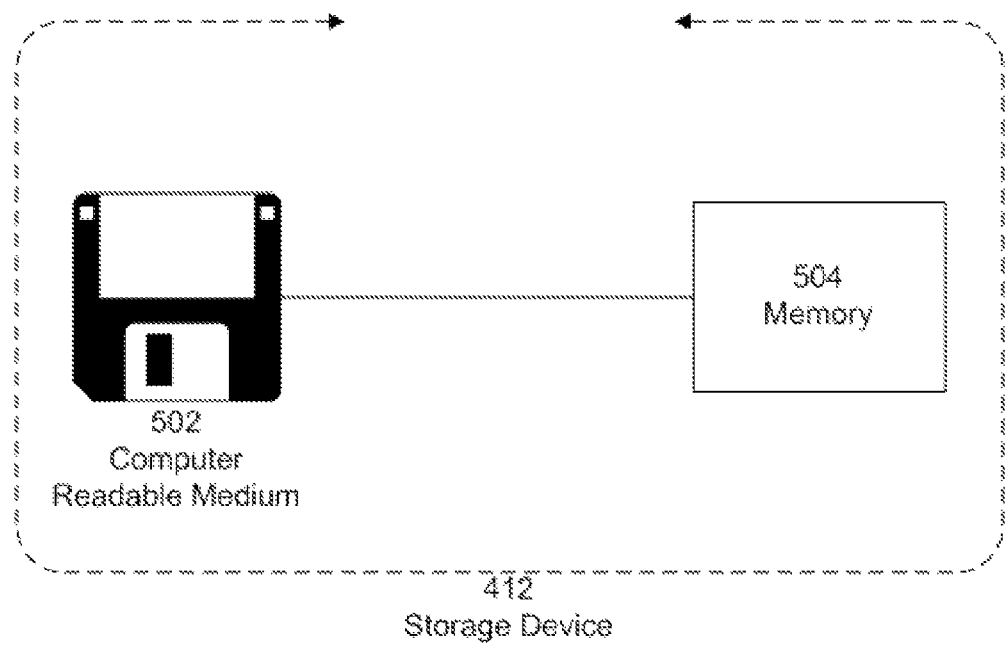
FIG. 6 is a schematic of a storage device 412.

The medium may, for example, be a disk 502 or flash memory as shown in FIG. 6. Typically, in operation, the processor causes data to be read from the nonvolatile recording medium into another memory 504 that allows for faster access to the information by the processor than does the medium. This memory is typically a volatile, random access memory such as a dynamic random access memory (DRAM) or static memory (SRAM). In one example, the computer-readable medium is a non-transient storage medium.

Referring again to FIG. 5, the memory can be located in storage 412 as shown, or in memory system 410. The processor 406 generally manipulates the data within the memory 410, and then copies the data to the medium associated with storage 412 after processing is completed. A variety of mechanisms are known for managing data movement between the medium and integrated circuit memory element and the invention is not limited thereto. The invention is not limited to a particular memory system or storage system.

The computer system may include specially-programmed, special-purpose hardware, for example, an application-specific integrated circuit (ASIC). Aspects of the invention can be implemented in software executed on hardware, hardware or firmware, or any combination thereof. Although computer system 400 is shown by way of example as one type of computer system upon which various aspects of the invention can be practiced, it should be appreciated that aspects of the invention are not limited to being implemented on the computer system as shown in FIG. 5. Various aspects of the invention can be practiced on one or more computers having a different architecture or components than that shown in FIG. 5.

It should also be appreciated that the invention is not limited to executing on any particular system or group of systems. Also, it should be appreciated that the invention is not limited to any particular distributed architecture, network, or communication protocol.

Various embodiments of the invention can be programmed using an object-oriented programming language, such as Java, C++, Ada, or C# (C-Sharp). Other object-oriented programming languages may also be used. Alternatively, functional, scripting, and/or logical programming languages can be used. Various aspects of the invention can be implemented in a non-programmed environment (e.g., documents created in HTML, XML or other format that, when viewed in a window of a browser program, render aspects of a graphical-user interface (GUI) or perform other functions). The system libraries of the programming languages are incorporated herein by reference. Various aspects of the invention can be implemented as programmed or non-programmed elements, or any combination thereof.

Various aspects of this invention can be implemented by one or more systems similar to system 400. For instance, the system can be a distributed system (e.g., client server, multi-tier system) comprising multiple general-purpose computer systems. In one example, the system includes software processes executing on a system associated with evaluating a subject having multiple sclerosis (MS), or at risk of developing MS according to various embodiments of the invention. Various system embodiments can execute operations such as administering an assessment of processes involved in learning and/or remembering visual information (e.g., Selective Reminding Test (SRT)), administering an assessment of visuospatial memory (e.g., Brief Visuospatial Memory Test (BVMT)), administering an assessment of complex scanning and/or visual tracking (e.g., Symbol Digit Modalities Test (SDMT), administering an assessment of one or more of auditory information processing speed, flexibility or calculation ability (e.g., Paced Auditory Serial Addition Test (PASAT)), or any combination of one, two, three, four, or more of the tests, as examples. The systems may permit physicians to access and manage such testing, specific patient information, patient responses, patient profiles, patient analysis, etc.

There can be other computer systems that perform functions such as evaluating additional parameters chosen from one or more of quality of life, neuropsychological evaluation, or memory function, where the system can administer and/or facilitate administration of testing to establish one or more of quality of life, neuropsychological evaluation, or memory function parameters, evaluate submitted additional parameters, establish reference values from a healthy subject or an average of healthy subjects, a subject at different time interval, e.g., prior to, during, or after the MS therapy, a group of MS patients having the same or different disease progressions, calculate a value of a composite parameter for a subject from an average value of one or more memory factors and one or more attention factors, calculating a value of the attention factor from a score of an average of the sum of an assessment of complex scanning and/or visual tracking and the average of at least two assessments of auditory information processing speed, flexibility or calculation ability, calculating a value of an attention factor based on determining $\{SMDT+[PASAT\ 3+PASAT\ 2]/2)\}/2$, wherein PASAT 3 represents a distinct execution of the PASAT test from PASAT 2, calculating a value for a verbal memory factor from the average of the sum of at least two assessments of processes involved in learning and/or remembering visual information, averaging SRT Total Learning and SET Delayed Recall values, calculating a value for a verbal memory factor based on determining (SRT Total Learning+

SRT Delayed Recall)/2, calculating a value for a visual memory factor from an average of at least two assessments of visuospatial memory, calculating a value for a visual memory factor based on determining (BVMT Total Recall+ BVMT Delayed Recall)/2, calculating a value for a memory factor from an average of a value of the verbal memory factor and a value of a visual memory factor, determining a reliability of a composite parameter, determining the reliability of the composite parameter to be at least one of 0.65, 0.69, 0.70, 0.75, 0.80, 0.85, and higher.

These systems can also be configured to manage administration of testing, accept as input results from testing, determine trends in evaluations, establish a statistical confidence measure based on input results, among other options. These systems can be distributed among a communication system such as the Internet. One such distributed network, as discussed below with respect to FIG. 7, can be used to implement various aspects of the invention.

Figure 7:
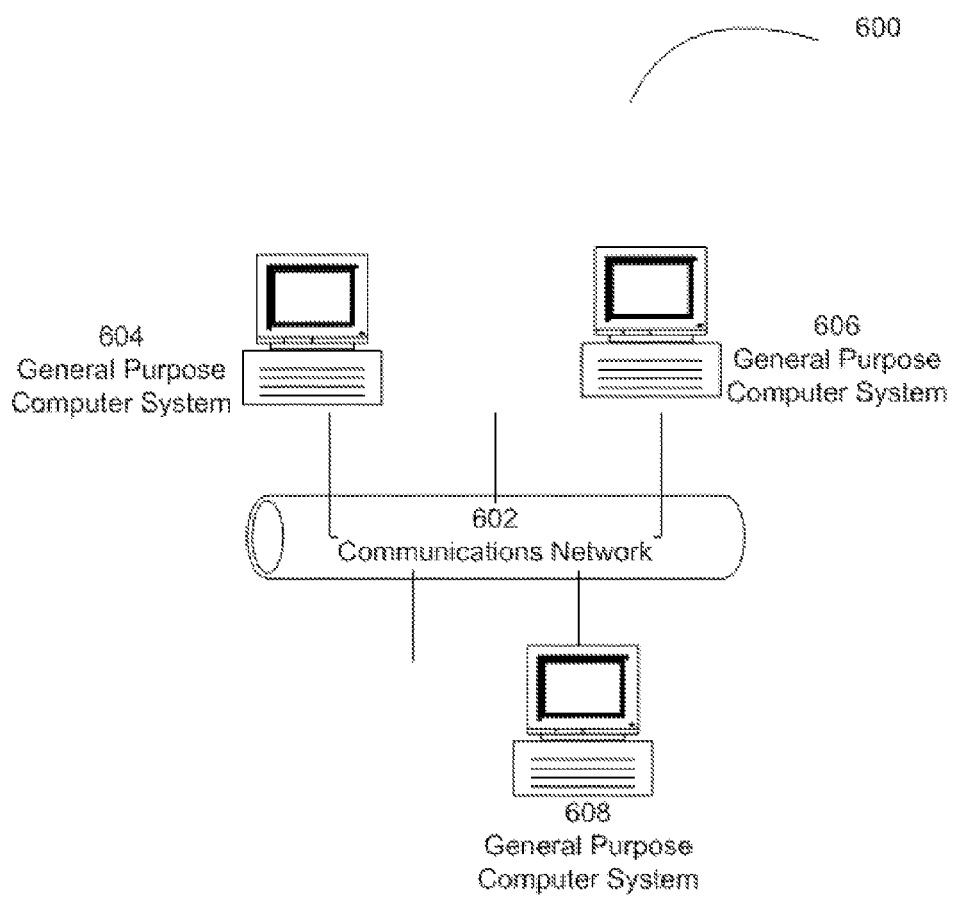
FIG. 7 shows an architecture diagram of an example distributed system 600

FIG. 7 shows an architecture diagram of an example distributed system 600 suitable for implementing various aspects of the invention. It should be appreciated that FIG. 7 is used for illustration purposes only, and that other architectures can be used to facilitate one or more aspects of the invention. System 600 may include one or more general-purpose computer systems distributed among a network 602 such as, for example, the Internet. Such systems may cooperate to perform functions related to evaluating a subject having multiple sclerosis (MS), or at risk of developing MS, treating a subject a subject having multiple sclerosis (MS), or a risk of developing MS, monitoring a subject having multiple sclerosis (MS), or at risk of developing MS, diagnosing or prognosing a subject having multiple sclerosis (MS), or at risk of developing MS, preventing MS in a subject having multiple sclerosis (MS), or at risk of developing MS, In an example of one such system, one or more users operate one or more client computer systems 604, 606, and 608 through which, for example, subjects can be administered a visual, audio, or other type of test to facilitate scoring of various factors, or users can enter testing results for subject, view reports on diagnosis and/or evaluation of treatment, view suggestions on alternative therapies, etc. It should be understood that the one or more client computer systems 604, 606, and 608 can also be used to access and/or update, for example, subject information, test results, potential therapies, etc. In one example, users interface with the system via an Internet-based user interface.

In another example, a system 604 includes a browser program such as the Microsoft Internet Explorer application program, Mozilla's FireFox, or Google's Chrome browser through which one or more websites can be accessed. Further, there can be one or more application programs that are executed on system 604 that perform functions associated with evaluating a subject having multiple sclerosis (MS), or at risk of developing MS according to various embodiments of the invention, treating, diagnosis, and/or monitoring the subject. For example, system 604 may include one or more local databases for storing, caching and/or retrieving subject information associated with testing, treating, monitoring, diagnosing MS, etc.

Network 602 may also include, one or more server systems, which can be implemented on general-purpose computers that cooperate to perform various functions including evaluating testing results, inputting testing results, determining composite parameter values for a subject, evaluating treatment options based on composite parameter values, suggesting alternative therapies for a subject based on composite parameter values, among other functions. System 600 may execute any number of software programs or processes and the invention is not limited to any particular type or number of processes. Such processes can perform the various workflows and operations discussed, and can also include, for example, operations for generating reports regarding determinations of one or more values for a composite parameter, communicating analysis of established values of the composite parameter, communicating evaluation or treatment of a subject to a report-receiving party or entity (e.g., a patient, a health care provider, a diagnostic provider, and/or a regulatory agency, e.g., the FDA), acquiring and storing values of a composite parameter including an attention factor and memory factor, in a subject (e.g., a patient, a patient group or a patient population), having multiple sclerosis (MS), or at risk for developing MS, prior to, during, and/or after the MS therapy, establishing and storing values of a composite parameter including an attention factor and memory factor, in a subject (e.g., a patient, a patient group or a patient population), having multiple sclerosis (MS), or at risk for developing MS, prior to, during, and/or after the MS therapy from input data and/or data received from other systems, among other examples.

Other features and embodiments of the invention include the following:

Additional Methods

In one aspect, the invention features a method of evaluating a subject having multiple sclerosis (MS), or at risk of developing MS, comprising: acquiring a value of a composite parameter from the subject, said composite parameter comprising an attention factor and a memory factor, thereby evaluating the subject, wherein responsive to a determination of the value of the composite parameter, the method further comprises one or more of: (i) identifying the subject as being in need of a first MS therapy or a second (alternative) MS therapy; (ii) identifying the subject as having an increased or a decreased response to a first MS therapy or a second (alternative) MS therapy; (iii) identifying the subject as being stable, showing an improvement in cognitive abilities, or showing a decline in cognitive abilities; (iv) diagnosing, and/or prognosing the subject; (v) selecting or altering the course of, an MS therapy or treatment, a dose, a treatment schedule or time course, and/or the use of an alternative MS therapy, in the subject; (vi) determining a time course of MS disease progression in the subject; (vii) administering a first MS therapy or a second (alternative) MS therapy to the subject; or (viii) administering to the subject a therapy for the management of cognitive and/or memory impairment.

In yet another aspect, the invention features a method of detecting and/or quantifying a cognitive impairment in a subject having a multiple sclerosis (MS), or at risk of developing the MS, comprising: acquiring a value of a composite parameter from the subject, said composite parameter comprising an attention factor and a memory factor, wherein responsive to a determination of the value of the composite parameter, the method further comprises one or more of: (i) identifying the subject as being in need of a first MS therapy or a second (alternative) MS therapy; (ii) identifying the subject as having an increased or a decreased response to a first MS therapy or a second (alternative) MS therapy; (iii) identifying the subject as being stable, showing an improvement in cognitive abilities, or showing a decline in cognitive abilities; (iv) diagnosing, and/or prognosing the subject; (v) selecting or altering the course of, an MS therapy or treatment, a dose, a treatment schedule or time course, and/or the use of an alternative MS therapy; (vi)

determining a time course of MS disease progression in the subject; or (vii) administering a first MS therapy or a second (alternative) MS therapy to the subject; or (viii) administering to the subject a therapy for the management of cognitive and/or memory impairment.

In another aspect, the invention features a method of treating or preventing one or more symptoms associated with multiple sclerosis (MS), in a subject having MS, or at risk for developing MS, comprising: acquiring a value of a value of a composite parameter from the subject, said composite parameter comprising an attention factor and a memory factor; and responsive to said value, administering to the subject an MS therapy, in an amount sufficient to reduce one or more symptoms associated with MS, wherein, in response to an increased value of said composite parameter relative to a reference value, the MS therapy is initiated or continued; and wherein, in response to a decreased value of said composite parameter relative to a reference value, the MS therapy is modified or an alternative MS therapy is used.

In yet another aspect, the invention features a method of evaluating or monitoring disease progression in a subject having MS, or at risk for developing MS, comprising: acquiring a value of a composite parameter from the subject, said composite parameter comprising an attention factor and memory factor; and comparing the value of the composite parameter from the subject to a reference value, wherein the value of the composite parameter differs according to the severity of MS, and an increase in the value of the composite parameter, relative to the reference value, is indicative of improved cognitive function in the subject.

Additional embodiments of the invention include one or more of the following:

In certain embodiments, the value of the composite parameter is lower in a patient having with secondary progressive multiple sclerosis (SPMS) compared to a patient with relapse remitting multiple sclerosis (RRMS). In certain embodiments, an increase in the value of the composite parameter, relative to the reference value, is indicative of improved cognitive function in the subject. In certain embodiments, a decrease in the value of the composite parameter, relative to the reference value, is indicative of decreased cognitive function in the subject. In certain embodiments, the value of the composite parameter is acquired by evaluating one, two, three, four or more attention and memory factors.

In certain embodiments, the memory factor is chosen from one or more verbal or visual memory factors. In certain embodiments, the attention and memory factors are obtained from administering one, two, three, four or more of: (i) an assessment of processes involved in learning and/or remembering visual information, (ii) an assessment of visuospatial memory, (iii) an assessment of complex scanning and/or visual tracking, or (iv) an assessment of one or more of auditory information processing speed, flexibility or calculation ability.

In certain embodiments, the method further comprises evaluating additional parameters chosen from one or more of quality of life, neuropsychological evaluation, or memory function.

In certain embodiments, the reference value is acquired from: a healthy subject or an average of healthy subjects; the subject prior to, during, or after the MS therapy; or a group of MS patients having the same or different disease progressions.

In certain embodiments, the value of the composite parameter is an average value of one or more memory factors and one or more attention factors.

In certain embodiments, the value of the attention factor is evaluated by obtaining a score of: the average of the sum of an assessment of complex scanning and/or visual tracking and the average of at least two assessments of auditory information processing speed, flexibility or calculation ability; or $\{SMDT+[PASAT\ 3+PASAT\ 2]/2)\}/2$.

In certain embodiments, the value of the verbal memory factor is evaluated by obtaining a score of: the average of the sum of at least two assessments of processes involved in learning and/or remembering visual information; or (SRT Total Learning+SRT Delayed Recall)/2.

In certain embodiments, the value of the visual memory factor is evaluated by obtaining a score of: the average of at least two assessments of visuospatial memory; or (BVMT Total Recall+BVMT Delayed Recall)/2. In certain embodiments, the value of the memory factor is the average of the value of the verbal memory factor and the visual memory factor.

In certain embodiments, the value of the composite parameter has a reliability of at least 0.65, 0.69, 0.70, 0.75, 0.80, 0.85 or higher.

In certain embodiments, the subject is a patient having one of: benign MS, relapse/remitting MS (RRMS), primary progressive MS, secondary progressive MS (SPMS), clinically isolated syndrome (CIS), or clinically defined MS (CDMS). In certain embodiments, the subject has quiescent RRMS or active RRMS. In certain embodiments, the subject has secondary progressive MS (SPMS). In certain embodiments, the method further comprises treating, or preventing in, the subject having multiple sclerosis MS one or more symptoms associated with MS by administering to a subject an MS therapy, in an amount sufficient to reduce one or more symptoms associated with MS. In certain embodiments, said treating or preventing comprises reducing, retarding or preventing, a relapse, or the worsening of a disability, in the MS subject.

In certain embodiments, the MS therapy comprises one or more of an IFN-β1 molecule; a polymer of glutamic acid, lysine, alanine and tyrosine; an antibody or fragment thereof against alpha-4 integrin; an anthracenedione molecule; a fingolimod; a dimethyl fumarate; an antibody to the alpha subunit of the IL-2 receptor of T cells; an antibody against CD52 or alemtuzumab; an inhibitor of a dihydroorotate dehydrogenase or teriflunomide; or an anti-LINGO-1 antibody. In certain embodiments, the IFN-β1 molecule comprises one or more of an IFN-β1a or IFN-β1-b polypeptide, a variant, a homologue, a fragment or a pegylated variant thereof. In certain embodiments, the MS therapy comprises an IFN-1b molecule; a polymer of glutamic acid, lysine, alanine and tyrosine; or the MS therapy comprises an alternative MS therapy chosen from an antibody or fragment thereof against alpha-4 integrin; a dimethyl fumarate' anthracenedione molecule; a fingolimod; a dimethyl fumarate; an antibody to the alpha subunit of the IL-2 receptor of T cells; or an anti-LINGO-1 antibody.

In certain embodiments, the method further comprises one or more steps of: performing a neurological examination, evaluating the subject's status on the Expanded Disability Status Scale (EDSS), or detecting the subject's lesion status as assessed using an MRI.

In certain embodiments, the subject is monitored in one or more of the following periods: prior to beginning of treatment; during the treatment; after the treatment has been administered; or at a first and second time points at least 1, 2, 3, 4, 5, or 6 months apart.

In certain embodiments, the method further comprises memorializing the value of the composite parameter, and/or providing a report comprising the memorialization.

Additional Systems and Computer-Implemented Methods

In another aspect, the invention features a system for evaluating disease progression in a subject having multiple sclerosis (MS), or at risk for developing MS, comprising: at least one processor operatively connected to a memory, the at least one processor when executing is configured to: establish a value of a composite parameter associated with the subject reflective of cognitive function, wherein the at least one processor is further configured to establish the value of the composite parameter responsive to establishing an attention factor value for the subject and a memory factor value for the subject; compare the value of the composite parameter from the subject to a reference value, and identify an indication of improved cognitive function in the subject in response to MS therapy, wherein identifying the indication of improved cognitive function includes detecting an increase in the value of the composite parameter, relative to the reference value; or identify an indication of decreased cognitive function in the subject in response to MS therapy, wherein identifying the indication of decreased cognitive function includes detecting a decrease in the value of the composite parameter, relative to the reference value.

In certain embodiments, the at least one processor when executing is configured to: compute an average value of one or more memory factors to determine the memory factor value and an average value of one or more attention factors to determine the attention factor value; and compute the composite parameter from a combination of the memory factor value and the attention factor value. In certain embodiments, the at least one processor when executing is configured to compute an average value of the sum of an assessment of complex scanning and/or visual tracking and the average of at least two assessments of auditory information processing speed, flexibility or calculation ability to determine at least a portion of the attention factor value for the subject. In certain embodiments, the at least one processor when executing is configured to compute the attention factor value based on determining a value for the equation ((Symbol Digit Modalities Test (SDMT) value+(Paced Auditory Serial Addition Test ("PASAT") value ("PASAT1")) and a second PASAT value ("PASAT2"))/2)/2.

In certain embodiments, the at least one processor when executing is configured to compute at least a portion of the value of the one or more memory factors based on the average of a sum of values determined for at least two assessments of processes involved in learning and/or remembering visual information. In certain embodiments, the at least one processor when executing is configured to compute at least a portion of the memory factor value based on determining a value for the equation (Selective Reminding Test ("SRT") Total Learning value+SRT Delayed Recall value)/2. In certain embodiments, the at least one processor when executing is configured to compute at least the portion of the value of the one or more memory factors based on an average of at least two assessments of visuospatial memory. In certain embodiments, the at least one processor when executing is configured to compute at least the portion of the memory factor value based on determining a value for the equation (Brief Visuospatial Memory Test ("BVMT") Total Recall value+BVMT Delayed Recall value)/2. In certain embodiments, the at least one processor when executing is configured to compute at least the portion of the memory factor value based on determining the average of the value of a verbal memory factor and a visual memory factor from the equation ((SRT Total Learning value+SRT Delayed Recall value)/2+(BVMT Total Recall value+BVMT Delayed Recall value)/2)/2.

In certain embodiments, the at least one processor when executing is configured to compute the composite value from the average of the value of the verbal memory factor and the visual memory factor averaged with the attention factor value calculated from the equation ((SDMT value+(PASAT1 and PASAT2)/2)/2. In certain embodiments, the at least one processor when executing is further configured to: compute a reliability value for the composite parameter, and evaluate the reliability value against a minimum threshold parameter including at least one of the threshold parameter set for at least 0.65, 0.69, 0.70, 0.75, 0.80, 0.85 or higher.

In certain embodiments, the at least one processor is configured to evaluate the composite parameter against a probabilistic model of a time course progression of disease effect on cognition for the subject, wherein the probabilistic model includes the reference value. In certain embodiments, the at least one processor is configured to generate the probabilistic model of the time course progression of the disease effect on cognition for the subject including a time course of the reference value. In certain embodiments, the at least one processor is configured to generate the probabilistic model from at least one population of: healthy subjects; a group of healthy subjects; the subject prior to, during, or after the MS therapy; a group of MS patients having the same disease progressions; a group of MS patients having the different disease progressions; a group of MS patients having the same or different disease progressions at different time intervals; a group of MS patients undergoing different MS treatments than the subject; or a group of MS patients undergoing a same MS treatment as the subject.

In certain embodiments, the at least one processor is configured to identify patients having similar MS disease progression from a model population. In certain embodiments, the at least one processor is configured to: compute a SRT Total Learning value, SRT Delayed Recall value, BVMT Total Recall value, BVMT Delayed Recall value to establish a memory factor portion for the reference value; compute a SDMT value, a first PASAT, a second PASAT value to establish an attention factor portion; and compute a combination of the memory factor portion and the attention factor portion to obtain the reference value.

In certain embodiments, the at least one processor when executing is further configured to: compute a reliability value for the reference value, and evaluate the reliability value against a minimum threshold parameter including at least one of the threshold parameter set for at least 0.65, 0.69, 0.70, 0.75, 0.80, 0.85 or higher. In certain embodiments, the at least one processor when executing is further configured to perform one or more of: comparing the value of the composite parameter from the subject to a reference value for a time parameter defined for a course of MS progression; identifying the subject as being in need of an MS therapy; recommending administration of an MS therapy; determining or altering a dosing of the MS therapy; determining or altering a schedule or a time course of the MS therapy; and recommending an alternative MS therapy.

In certain embodiments, the at least one processor when executing is configured to determine the attention and memory factors, at least in part, from administering, or on the results from administration, of one, two, three, four or more of: (i) an assessment of processes involved in learning and/or remembering visual information, (ii) an assessment of visuospatial memory, (iii) an assessment of complex scanning and/or visual tracking, or (iv) an assessment of one or more of auditory information processing speed, flexibility or calculation ability. In certain embodiments, the at least one processor when executing is further configured to: capture a plurality of values of the composite parameter for the subject over time, and generate a model of the time course progression of the composite parameter, wherein the model is reflective of a disease state of the subject having MS.

In one aspect, the invention features a computer implemented method for evaluating disease progression in a subject having multiple sclerosis (MS), or at risk for developing MS, the method comprising: establishing, by a computer system, a value of a composite parameter associated with the subject reflective of cognitive function, wherein establishing the value of the composite parameter includes establishing an attention factor value for the subject and a memory factor value for the subject; comparing, by the computer system, the value of the composite parameter from the subject to a reference value, and identifying, by the computer system, an indication of improved cognitive function in the subject in response to MS therapy, wherein identifying the indication of improved cognitive function includes detecting an increase in the value of the composite parameter, relative to the reference value; or identifying, by the computer system, an indication of decreased cognitive function in the subject in response to MS therapy, wherein identifying the indication of decreased cognitive function includes detecting a decrease in the value of the composite parameter, relative to the reference value.

In certain embodiments, establishing an attention factor value for the subject and a memory factor value for the subject includes: computing an average value of one or more memory factors to determine the memory factor value; computing an average value of one or more attention factors to determine the attention factor value; and computing the composite parameter from a combination of the memory factor value and the attention factor value. In certain embodiments, the method further comprises computing an average value of the sum of an assessment of complex scanning and/or visual tracking and the average of at least two assessments of auditory information processing speed, flexibility or calculation ability to determine at least a portion of the attention factor value for the subject. In certain embodiments, establishing the attention factor value for the subject includes computing the attention factor value based on determining a value for the equation ((Symbol Digit Modalities Test (SDMT) value+(Paced Auditory Serial Addition Test ("PASAT") value ("PASAT1")) and a second PASAT value ("PASAT2"))/2)/2.

In certain embodiments, the method further comprises computing at least a portion of the value of the one or more memory factors based on the average of a sum of values determined for at least two assessments of processes involved in learning and/or remembering visual information. In certain embodiments, the method further comprises computing at least a portion of the memory factor value based on determining a value for an equation (Selective Reminding Test ("SRT") Total Learning value+SRT Delayed Recall value)/2. In certain embodiments, computing at least the portion of the value of the one or more memory factors based on the average of the sum of values determined for at least two assessments of processes involved in learning and/or remembering visual information includes computing at least the portion of the value of the one or more memory factors based on an average of at least two assessments of visuospatial memory.

In certain embodiments, computing at least the portion of the memory factor value includes computing at least the portion of the memory factor value based on determining a value for the equation (Brief Visuospatial Memory Test ("BVMT") Total Recall value+BVMT Delayed Recall value)/2. In certain embodiments, computing at least the portion of the memory factor value includes determining the average of the value of a verbal memory factor and a visual memory factor from the equation ((SRT Total Learning value+SRT Delayed Recall value)/2+(BVMT Total Recall value+BVMT Delayed Recall value)/2)/2. In certain embodiments, establishing the value of the composite value includes computing the composite value from the average of the value of the verbal memory factor and the visual memory factor averaged with the attention factor value calculated from the equation ((SDMT value+(PASAT1 and PASAT2)/2)/2.

In certain embodiments, the method further comprises computing a reliability value for the composite parameter, and evaluating the reliability value against a minimum threshold parameter including at least one of the threshold parameter set for at least 0.65, 0.69, 0.70, 0.75, 0.80, 0.85 or higher.

This invention is further illustrated by the following examples which should not be construed as limiting. The contents of all references, figures, sequence listing, patents and published patent applications cited throughout this application are hereby incorporated by reference.

EXEMPLIFICATION

Cognitive impairment is common in MS patients, with frequencies ranging from 40-75% reported in clinical samples (Rao et al. (1995) *Curr Opin in Neurol* 8: 216-220; Fischer et al. (1994) *Neurorehabil Neural Repair* 8: 151-164; Lyon-Caen et al. (1986) *Arch Neurol* 43: 1138-1141; Peyser et al. (1980) *Arch Neurol* 37: 577-579) and meta-analyses (Wishart et al. (1997) *Journal of Clinical and Experimental Neuropsychology* 19: 810-824; Thornton et al. (1997) *Neuropsychology* 11: 357-366; Prakash et al. (2008) *Multiple Sclerosis* 14: 1250-1261), with estimates varying according to the definition of cognitive impairment. Processing speed and learning/memory are the domains identified as most likely to be impaired in individual MS subjects with frequency rates estimated at approximately 52% and 54%, respectively (Rao et al. (1991) *Neurology* 41: 685-91; Benedict et al. (1996) *Psychological Assessment* 8: 145-153), and may co-occur or be observed independently. Cognitive impairments in acquired visual and verbal memory; working memory; executive functions, e.g., planning, organizing, and initiation; perceptual processing; fluency; visuospatial perception; speed; and concept formation are also commonly associated with MS (Chiaravalloti and DeLuca (2008) *The Lancet Neurology*, Volume 7 (12):1139-1151).

Loss of cognitive function occurs early on in active MS (Cadavid et al. (2011) *Multiple Sclerosis Journal*, 17: 1113-1121), and has been shown to significantly impact numerous areas of daily life including, employment, social and vocational activities, household activities, sexual functioning, family activities, overall quality of life, and psychiatric health (Rao et al, ((1991) *Neurology* 41(5):685-691). These cognitive impairments are relatively independent of the MS associated motor impairments ((Chiaravalloti and DeLuca (2008) supra). A pharmaceutical therapy that improved cognitive functioning in MS patients would therefore be of considerable value in the overall management of MS symptoms. However, in order to assess the effectiveness of pharmaceutical interventions, reliable and valid indices of meaningful cognitive change are required.

The Multiple Sclerosis Functional Composite (MSFC) has been deemed a clinically meaningful measure of disability in MS patients (Polman et al. (2010) Neurology, 74: 8-S15). However, while the measure has been shown to be sensitive to neurologic deterioration in general, it was not designed to monitor cognitive improvement or deterioration out of the context of more general improvement or decline. Further, the MSFC is lacking any measure of learning and memory, and is thus inadequate as a composite representation of cognitive functioning in MS patients who present with cognitive impairment in learning and memory, but not processing speed. In addition, the MSFC is further disadvantageous as it consists of a lengthy battery of tests, which must be administered by a neuropsychologist. Adequate assessment of MS cognitive impairment is confounded by the fact that the severity of cognitive disability in MS can be subtle to moderate, and the occurrence and patent of cognitive dysfunction are variable.

A composite endpoint which summarizes multiple domains of observations into a single index of overall functioning offers advantages, including increased sensitivity, greater statistical power and smaller sample size, greater simplicity in summarizing treatment effects, and relating the relevance of those effects. The current example establishes the sensitivity to impairment, reliability, validity, and psychometric properties of a cognitive composite parameter for use in patient evaluation and research on pro-cognitive pharmaceutical interventions in the MS population.

Example 1

Construction of MS Cognitive Composite Parameter

Cognitive Test Selection

The individual tests selected as component measures of the final composite parameter included broadly the Paced Auditory Serial Addition Test (PASAT), Selective Reminding Test (SRT), Symbol Digit Modalities Test (SDMT), and the Brief Visuospatial Memory Test-Revised (BVMT-R). Specifically, the six-trial format of the SRT was selected with Hannay and Levin's word lists for adults, forms 1 and 3. Two alternate versions (PASAT 2" and PASAT 3") were selected for the PASAT; and the oral version of the SDMT was selected. The PASAT and SDMT are measures of working memory and processing speed, the SRT is a measure of auditory/verbal learning and memory, and the BVMT-R is a measure of visual learning and memory. Component tests were selected based on the sensitivity of the proposed component tests to memory and processing speed deficits in MS patients, test-retest reliability, the availability of multiple alternate forms for longitudinal studies, suitability for administration by trained clinical staff, and the potential for use in cross-cultural settings.

The individual component tests have been used in multiple clinical trials for evaluation of cognitive disabilities and the assessment of therapeutic regimens on cognitive function. For example, the PSAT has been used to evaluate the effect of Avonex® on cognitive impairment (Fischer et al, (2000) Ann Neurol, 48: 885-92) and the effect of Avonex® on cognitive impairment in SPMS subjects in the IMPACT trial (FIG. 1A; Cadavid et al, AAN 2010 Toronto); the effect of Rituxan® in PPMS subjects in the OLYMPUS trial (FIG. 1B); and the effect of Tysabri® on cognitive impairment in the AFFIRM trial. The SDMT has been used to evaluate the effect of tysabri on cognitive impairment in the STRATA trial (Morrow, ECTRIMS, 2009). In addition, the SDMT has been used evaluate the effect of acute relapses on cognition in MS (Morrow et al, (2001) J Neurol, 258: 1609).

Participants

Participants were recruited from four centers in New York and New Jersey, each recruiting 15 patients with a documented history of Relapsing-Remitting or Secondary Progressive MS. Participants were included regardless of MS severity, the presence of cognitive impairment, or duration of illness; so as to be representative of the general MS patient population. Exclusion criteria included physical or sensory impairment that might preclude completion of cognitive test protocols, untreated major depressive disorder, untreated anxiety disorder, history of severe psychiatric illness, severe traumatic brain injury, a medical illness that would preclude successful completion of the assessments, history of serious infection within 2 months prior to Study Day 1, use of marijuana within 2 months prior to Study Day 1 or at any time during the study, or relapse within two months of start date. All patients were native English speakers.

Demographic characteristics of the sample identified the group as typical of clinical MS populations. The group was comprised of 43 women (72%) and 16 men (28%) recruited from lists of patients diagnosed with MS according to McDonald criteria in 4 northeastern U.S. clinics, with an average age of 47.9 (sd=7.9; range=26-61). Except for one subject who was excluded because of the onset of clinically significant symptoms of depression following Study Day 1, all patients were neurologically and psychiatrically stable for the duration of the study. A majority (77%) were receiving disease modifying therapy. Average time since diagnosis was 13.2 years (d.s.=8.5; range=1-33). Similar to reported studies of other clinical MS populations, the majority (87%) were Caucasian, with 5% identifying as African-American, 5% as Hispanic, and 3% as Other. Approximately 77% of participants had a diagnosis of Relapsing-Remitting MS and 23% a diagnosis of Secondary Progressive MS. The median EDSS was 2.5 and the mode was 2. Only 2% were not high school graduates, with 27% having a high school degree or GED, 18% an Associates Degree, 28% a Bachelors Degree, 21% a Masters Degree, and 5% an advanced degree.

Assessment Procedures

Participants were assessed at two time points, approximately 45 days apart. Each participant completed the SDMT Oral Version, PASAT, BVMT-R, and SRT on each occasion. Order of test administration was the following: SRT Learning Trials, SDMT, PASAT 3- and 2-second trials, the Wechsler Adult Intelligence Scale-IV Matrix Reasoning subtest, SRT Delayed Recall, and BVMT-R Delayed Recall. The Wechsler Adult Intelligence Scale-IV Matrix Reasoning subtest was included as an estimate of premorbid intelligence, and to allow the desired interval between learning and delay trials on memory measures. The test instruments used for each component test are described above. Total time for administration was approximately 30 minutes.

Equivalent alternate forms were used to minimize form-specific practice effects. Forms were administered in the same order to all subjects. Results were scored by a central rater to ensure consistency and subsequently double entered into an electronic database. For the SDMT, the original WPS-published form was administered at Study Day 1 and the Rao's Form 2 was administered at Study Day 2 (Smith et al. (1982) *Symbol digit modalities test: Manual. Los Angeles: Western Psychological Services*; Rao et al. (1991) *Neurology* 41: 685-691).

Test Instruments

Symbol Digit Modalities Test (SDMT)

In this measure of processing speed and working memory, the subject is given 90 seconds to pair specific numbers with given geometric figures based on a reference key using an oral response, to limit problems due to dexterity in MS patients (Rao S M. Neuropsychological Screening Battery for Multiple Sclerosis: National Multiple Sclerosis Society; 1991b). At Study Day 1 the original, WPS-published form was administered and at Visit 2 Rao's Form 2 was administered ((Smith A. Symbol digit modalities test: Manual. Los Angeles: Western Psychological Services; 1982); (Rao S M. A Manual for the Brief, Repeatable Battery of Neuropsychological Tests in Multiple Sclerosis: National Multiple Sclerosis Society; 1991a)).

Paced Serial Addition Test (PASAT)

First developed by Gronwall to assess patients recovering from concussion, the PASAT requires patients to monitor a series of 61 audiotaped digits while adding each consecutive digit to the one immediately preceding it (Gronwall DMA. Perceptual and Motor Skills 1977; 44:367-73). The number of intervals and presentation rates were subsequently modified by Rao and colleagues calling for two trials, with inter-stimulus intervals of 3 and 2 seconds, respectively (Rao S M. A Manual for the Brief, Repeatable Battery of Neuropsychological Tests in Multiple Sclerosis: National Multiple Sclerosis Society; 1991a). Rao's Form 1 and 2 were administered at Study Day 1 and 2, respectively.

Selective Reminding Test

The history of this test begins with the work of Buschke et al who conducted research in the area of anterograde amnesia (Buschke F. Neurology. 1974; 24:1019-25). After the examiner reads a list of 12 target words on an initial learning trial, the test-taker is asked to try to repeat the entire list. On 5 subsequent learning trials, the SRT requires the experimenter to repeat only target words not recalled by the subject on the previous trial, and test-taker is asked to repeat the entire list. A delayed recall trial is included. Hannay and Levin's word lists for adults, Forms 1 and 3, were selected for this study based on available research (Hannay H J, Levin H S. Journal of clinical and experimental neuropsychology. 1985; 7).

Brief Visuospatial Memory Test-Revised

The Brief Visuospatial Memory Test-Revised (BVMT-R) is based on an initial effort to develop equivalent alternate form visual memory tests ((Benedict R H B. Neuropsychological Rehabilitation. 1993; 3:37-51); Benedict R H B. The Clinical neuropsychologist. 1995; 9)). In the revised version, the BVMT-R includes three 10-sec exposures to the stimulus (Benedict R H B. Brief Visuospatial Memory Test-Revised: Professional Manual. Odessa, Fla.: Psychological Assessment Resources, Inc.; 1997); (Benedict R H B. Psychological Assessment. 1996; 8:145-53)). After each exposure, the subject is asked to reproduce the matrix with using a pencil on a blank sheet of paper. Further, there is extensive research showing that all 6 forms of the test are of equivalent difficulty. Variables of interest in the current study were the Total Learning and Delayed Recall scores.

Memory Functioning Questionnaire

The Memory Functioning Questionnaire was designed to examine self-reported memory complaints (Gilewski M J. Psychology and aging. 1990; 5). It consists of 64 items addressing memory difficulty and frequency of forgetting, presented in 7 sections, each rated on a 7-point scale.

MS Neuropsychological Questionnaire

The MSNQ is a 15-item report schedule with versions developed both for patient- and informant-reports of cognitive and neuropsychiatric symptoms commonly observed in the MS population (Benedict R H. Multiple sclerosis. 2003; 9).

MS Quality of Life-54

The MSQOL-54 was developed by combining the most widely utilized generic measure of quality of life in the world, the SF-36, with additional items specific to MS.

Data Analysis

Analyses were completed using SPSS software. Two participants did not complete PASAT 2" at the initial visit after becoming overly frustrated. All raw scores were converted into demographically adjusted z scores using a single peer-reviewed US-database of control subjects similar in age, gender and education to the study group, which (Strober et al. (2009) *Mult Sclerosis*, 15: 1077-1084) were used for all analyses. Reliability was investigated using Pearson r correlations. Based on a priori assumptions based on existing literature (see e.g., Lezak et al., 2006, the PASAT and SDMT were combined into a processing speed (PS) factor and the SRT and BVMT-R combined into a learning and memory (LM) factor, which were examined using loadings on factor analysis as detailed below. The factors and composite parameter per se were constructed according to clinical usage as detailed below. An a priori cutoff of 0.70 was established as indicative of minimally acceptable reliability.

Component Measurements

Each component measure revealed sensitivity to cognitive impairment in the clinical sample. Standardized summary scores for cognitive indices identified as clinically sensitive by Strober et al. (see Strober et al. (2009) *Mult Sclerosis*, 15: 1077-1084) were computed based on that researcher's normative control data, which included all the measures of interest. Average performance across subtests was well below the control z score mean of 0 and ranged from −0.62 to −1.7 (Table 1). Prevalence of impairment as defined by a score of −1.5 or −1.0 standard deviations below the control mean or greater, ranged from 26% to 54% for the former and from 36% to 61% for the latter (Table 1). Each component measure also displayed good test-retest reliability as shown in Table 2.

The standardized summary scores were entered into a factor analysis. Eigenvalues of 4.43 and 1.04 identified two factors accounting for a total of 78% of the variance. All combinations of estimation method (principal axis factoring, maximum likelihood), rotation procedure (orthogonal vs. oblique), and extraction criteria (all factors with eigen values >1 vs. only the first two factors) were explored in order to explore the stability of the factors analysis. Varimax rotation with Kaiser normalization identified factor one as comprised of loadings of SRT Total Learning and Delayed Recall and BVMT-R Total Learning and Recall, with loadings ranging from 0.74 to 0.85 (Table 3). Factor 2 was comprised of SDMT, PASAT 3" and PASAT 2" (also referred to herein as PASAT 3 and PASAT 2, respectively) with loadings ranging from 0.57 to 0.95. These factors were labeled Learning and Memory (LM) Factor and Processing speed (PS) Factor, accordingly.

TABLE 1

Average Performances and Frequency of Cognitive Impairment on Individual Component Measures, Relative to Normative Control.

| Measure | Mean Z Score | % < −1.5 Std Dev |
|---|---|---|
| SDMT | −1.1 | 36 |
| PASAT 3 | −.7 | 27 |
| PASAT 2 | −.62 | 26 |
| SRT Total | −.75 | 29 |
| SRT Delay | −.80 | 34 |
| BVMT-R Total | −1.3 | 53 |
| BVMT-R Delay | −1.7 | 54 |

TABLE 2

Reliability for Individual Component Measures.

| Measure | Pearson r |
|---|---|
| SDMT | 0.88 |
| PASAT 3 | 0.85 |
| PASAT 2 | 0.87 |
| SRT Total Recall | 0.70 |
| SRT Delayed Recall | 0.62 |
| BVMT-R Total Recall | 0.82 |
| BVMT-R Delayed Recall | 0.83 |

TABLE 3

Rotated Component Matrix - Principal Component Analysis, Rotation Method: Varimax with Kaiser Normalization.

| | Component | |
|---|---|---|
| Factor | 1 | 2 |
| SDMT | 0.586 | 0.567 |
| PASAT 3" | 0.308 | 0.891 |
| PASAT 2" | 0.178 | 0.942 |
| SRT Learning | 0.744 | 0.420 |
| SRT Delayed Recall | 0.831 | 0.099 |
| BVMT-R Total Learning | 0.854 | 0.280 |
| BVMT-R Delayed Recall | 0.817 | 0.295 |

Factor Construction

The standardized summary scores were entered into a factor analysis. Eigen values of 4.43 and 1.04 identified two factors accounting for a total of 78% of the variance. Varimax rotation with Kaiser normalization identified factor 1 as comprised of loadings of SRT Total Learning, SRT Delayed Recall, BVMT-R Total Learning, and BVMT-R Recall, with loadings ranging from 0.74 to 0.85. Factor 2 was comprised of SDMT, PASAT 3", and PASAT 2", with loadings ranging from 0.57 to 0.95. Factor 1 was labeled as learning and memory (LM) factor and factor 2 as the processing speed (PS) factor.

Figure 2:
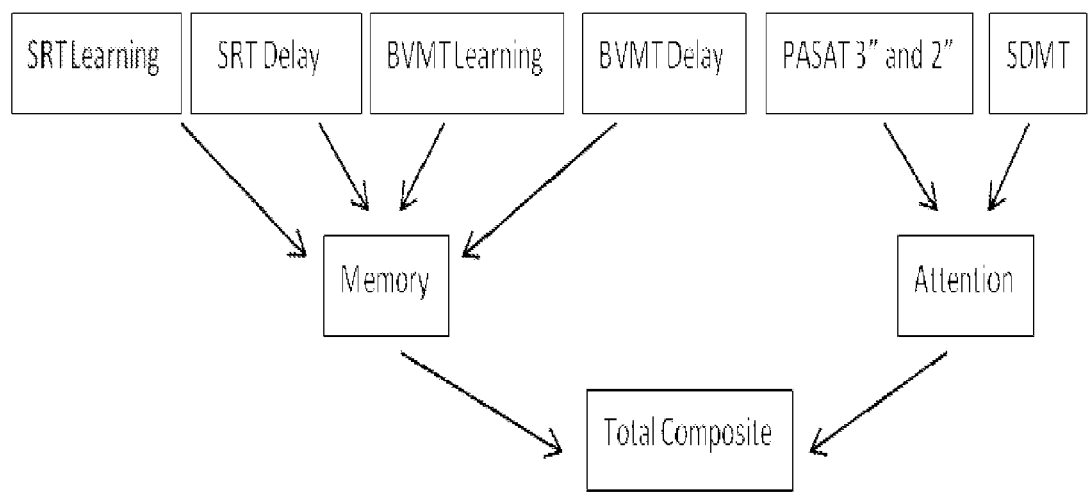
FIG. 2 is a diagram illustrating the methodology of constructing the composite parameter. The composite parameter is constructed by averaging the learning and memory (LM) factor and the processing speed (PS) factor. The LM factor is the average of the standard scores of the SRT Total Learning, SRT Delayed Recall, BVMT-R Total Learning, and BVMT-R Recall factors. The PS factor is the average of the two PASAT total scores (i.e., PASAT 3" and PASAT 2") subsequently averaged with the SDMT score.

The LM factor was constructed by averaging the standard scores for the 4 component indices (SRT Total Learning, SRT Delayed Recall, BVMT-R Total Learning, and BVMT-R Recall), thus giving equal weightings both to verbal and visual memory as well as to both learning and delayed recall scores. This plan was in keeping with each indices' roughly equivalent sensitivity to cognitive impairment in MS patients as detailed by Strober et al. (see Strober et al. (2009) *Mult Sclerosis*, 15: 1077-1084). For the PS composite, the two PASAT total scores (PASAT 3" and PASAT 2") were averaged and then subsequently averaged with the SDMT score, so as to give equal weightings to these different paradigms (PASAT 3" and PASAT 2"), as well as to reflect Strober's finding that the SDMT has relatively greater sensitivity to cognitive impairment (see Strober et al. (2009) *Mult Sclerosis*, 15: 1077-1084). A total composite was constructed by averaging the LM and PS composites with equal weighting. FIG. 2 diagrams the methodology of the total composite parameter construction.

Evaluation of the Factors and Composite Parameter

The sensitivity of the factors and the composite parameter to impairment was evident in the mean z scores ranging from z=−1 to z=−1.8 (Table 4), with the frequency of impairment being comparable to the numerous previously reported studies. Reliability of the factors and the composite parameter were considered excellent, with greater reliability associated with the composite score as reported in Table 5.

TABLE 4

Severity and Frequency of Impairment by MS Subtype for Factor Scores and the Composite Parameter Score.

| Factor | Mean Z Score | % < −1.5 Std Dev | % < −1 Std Dev |
|---|---|---|---|
| Processing Speed | −1.0 | 34 | 48 |
| Memory | −1.8 | 57 | 64 |
| Composite | −1.7 | 62 | 77 |

TABLE 5

Reliability for Factor scores and the Composite Parameter Score.

| Index | Pearson r |
|---|---|
| Learning and Memory Factor | 0.86 |
| Processing Speed Factor | 0.89 |
| Composite | 0.91 |

Psychometric characteristics of the composite parameter score were also analyzed, as it was anticipated that the measure will be used as an endpoint in pharmaceutical trials. As illustrated in Table 6, the composite parameter score showed good sensitivity to impairment particularly given that the sample is a clinical one, as indicated by the mean z score of −1.1 at Visit 1 and the normal distribution. A practice effect of 0.35 standard deviation was evident at Visit 2, although the strong reliability demonstrated by the composite score indicates that this is not an obstacle to detecting change in cognitive functioning in a pharmaceutical trial. Moreover, this retest effect is consistent with similar effects previously reported (see summary, Spreen and Strauss).

TABLE 6

Psychometric Characteristics of the Composite Parameter at Visit 1 and Visit 2.

| Statistic (Z scores) | Composite Score: Visit 1 | Composite Score: Visit 2 |
|---|---|---|
| Mean | −1.1 | −.75 |
| St Dev | 1.3 | 1.1 |
| St Error of Mean | .17 | .14 |
| Range | −4.1 to 1.3 | −3.1 to 1.2 |
| Skewness | −.37 | −.35 |
| Kurtosis | −.61 | −.77 |

To examine the clinical character of the composite parameter score, the severity and frequency of impairment were compared across the Relapsing-Remitting MS (RRMS) and Secondary Progressive MS subgroups (SPMS). As would be expected, those participants with Secondary Progressive MS had cognitive impairment of greater severity and were more frequently impaired on both composites and on the composite parameter score as shown in Table 7. Reliability scores according to MS subtype were excellent, with Secondary Progressive MS participants generally demonstrating somewhat greater reliabilities as shown in Table 8.

TABLE 7

Severity and Frequency of Impairment by MS Subtype for Factor scores and the Composite Parameter Score.

| Factor | MS Type | Mean Z Score | % < −1.5 Std Dev | % < −1 Std Dev |
|---|---|---|---|---|
| Processing | RR | −1.0 | 34 | 48 |
| Speed | SP | −1.8 | 62 | 62 |
| Learning and | RR | −.96 | 33 | 42 |
| Memory | SP | −1.8 | 57 | 64 |
| Composite | RR | −.96 | 37 | 39 |
| Endpoint | SP | −1.7 | 62 | 77 |

TABLE 8

Reliability coefficients for the Factor and Composite Parameter Scores Reliabilities by MS Subtype group

| Factor | MS Type | Pearson r |
|---|---|---|
| Processing | RR | 0.88 |
| Speed | SP | 0.90 |
| Learning and | RR | 0.82 |
| Memory | SP | 0.91 |
| Composite | RR | 0.90 |
| Endpoint | SP | 0.93 |

The study further evaluated the relationships between the composite endpoint parameter and the patient recorded outcomes (PROs), including the Mental Competent Summary (MSQOL (SF-36)), the Memory Functioning Questionnaire, (MFQ), and the Multiple Sclerosis Neuropsychological Questionnaire (MSNQ) (Table 9), and across the Relapsing-Remitting MS and Secondary Progressive MS subgroups as shown in Tables 10-12, as MSQOL, MFQ, and MSNQ could potentially serve as co-primary endpoints to the composite endpoint parameter in a clinical trial setting. PROs in both RRMS and SPMS showed excellent reliability. However, the PROs on SPMS subjects were found to be reliable but not valid. Unlike subject reports, the MSNQ informant reports alone were found to be reliable because they correlated with actual cognitive performance on the objective test with the cognitive composite battery.

TABLE 9

Test-Retest Correlations for Patient (PROs) or Informant (IROs) reported outcomes. All tests were found to be reliable based on high Pearson r values.

| Subtest | Pearson r |
|---|---|
| MFQ General Forgetting | .89 |
| MSQOL (Physical Health) | .88 |
| MSQOL (Mental Health) | .87 |
| MSNQ-Patient | .81 |
| MSNQ-Informant | .88 |

TABLE 10

RRMS versus SPMS Reliabilities for PROs. All tests were found to be reliable based on high Pearson r values, both in RRMS and SPMS.

| Subtest | MS TYPE | Pearson r with Composite |
|---|---|---|
| MFQ General Forgetting | RR | 0.88 |
| | SP | 0.87 |
| MSQOL (Physical Health) | RR | 0.94 |
| | SP | 0.94 |
| MSQOL (Mental Health) | RR | 0.92 |
| | SP | 0.92 |
| MSNQ-Patient | RR | 0.75 |
| | SP | 0.92 |
| MSNQ-Informant | RR | 0.86 |
| | SP | 0.75 |

TABLE 11

RRMS vs. SPMS Correlation: PROs with Cognitive Composite Parameter 1. Notice that only the MSNQ-informant showed a correlation with the actual cognitive performance.

| Subtest | r with Composite | MS TYPE | Pearson r with Composite |
|---|---|---|---|
| MFQ General Forgetting | 0.08 | RR | 0.14 |
| | | SP | −0.05 |
| MSQOL (Physical Health) | 0.16 | RR | 0.36 |
| | | SP | −0.36 |
| MSQOL (Mental Health) | 0.17 | RR | 0.35 |
| | | SP | −0.40 |
| MSNQ-Patient | −0.04 | RR | −0.19 |
| | | SP | 0.35 |
| MSNQ-Informant | −0.33 | RR | −0.37 |
| | | SP | −0.21 |

TABLE 12

RRMS vs. SPMS Correlation: PROs with Cognitive Composite Parameter 2. Notice that the patient reported outcomes did correlate with actual performance in RRMS but not in SPMS. Only the informant reports did correlate with actual performance in SPMS.

| Subtest | r with Composite | MS TYPE | Pearson r with Composite |
|---|---|---|---|
| MFQ General Forgetting | 0.20 | RR | 0.39 |
| | | SP | −0.11 |
| MSQOL (Physical Health) | 0.27 | RR | 0.44 |
| | | SP | −0.16 |
| MSQOL (Mental Health) | 0.22 | RR | 0.35 |
| | | SP | −0.15 |
| MSNQ-Patient | −0.20 | RR | −0.38 |
| | | SP | 0.13 |
| MSNQ-Informant | −0.39 | RR | −0.40 |
| | | SP | −0.37 |

Evaluation of Composite Parameter Endpoint

This study established the reliability of the proposed composite parameter for MS generally and for SPMS patients specifically. The composite parameter endpoint identified 62% to 77% of patients as having clinically significant cognitive impairment, which is similar to estimated rate of 55 to 75% prevalence reported in clinical samples using more comprehensive test batteries (see, Rao et al. (1995) *Curr Opin in Neurol*, 8: 216-20; Fischer et al. (1994) *Neurorehabil Neural Repair*, 8: 151-164; Lyon-Caen et al. (1986) *Arch Neurol*, 43(11):1138-1141; Edwards et al. (1980) *Arch Neurol*, 37: 577-579). Further, the PS and LM composites revealed sensitivities of 48% and 68%, respectively, which are similar to previously reported clinical sample estimates of 52% and 54% (see, Rao et al. (1991) *Neurology,* 41: 685-91; Benedict et al. (1996) *Psychological Assessment* 8: 145-153). Moreover, the frequency of impairment in the borderline or lower ranges identified by the Composite endpoint was maintained or increased modestly relative to the LM and PS composites, indicating that in this battery multidimensional assessment is likely preferable to individual domains for a pharmaceutical trial in which change in generalized cognitive ability is of interest. In this light, it is noted that findings of impairment in multiple domains if preferable to single domains in diagnosis of a cognitive impairment syndrome. Further, the Composite endpoint revealed greater frequency of impairment in patients with SPMS vs. RRMS, in keeping with the greater disease severity associated with the former population as documented in numerous research studies ((Benedict R H B. Journal of the International Neuropsychological Society. 2006; 12:549-58); Strober L. Multiple sclerosis. 2009; 15(9):1077-8); DeLuca J. Journal of clinical and experimental neuropsychology. 2004; 26(4):550-62)). This observation further supports the composite parameter endpoint as a reasonable surrogate in regard to sensitivity to cognitive impairment in MS compared to larger, broader test batteries. Study completion was excellent and supporting its use in multicenter trials.

In addition, the composite parameter demonstrated excellent test-retest reliability with a Pearson r value of 0.91, which was better than or similar to reports for the component subtests; although this was not unexpected given that an increased number of observations can provide a more stable basis for improved reliability. The composite parameter also demonstrated a normal distribution with no evidence of significant skew or kurtosis and a standard deviation close to that of a non-impaired population ($z=1.3$ for Visit 1; $z=1.1$ for Visit 2), an important feature for estimating sample sizes for large pharmaceutical trials. Similarly, the standard error of the mean of the composite parameter score was small compared to the standard deviation, indicating excellent potential for accuracy in assessment of each patient. Patient reported outcomes were not accurate predictors of objective measures of cognitive function.

Importantly, the psychometric methodology for establishing the PS and LM composites was strongly supported. Even in this relatively small sample size, factor analysis identified two and only two factors which, upon inspection, were comprised of the proposed component subtests in the respective cognitive domains. Within each cognitive domain, the SDMT showed somewhat greater sensitivity than the PASAT, and the BVMT-R showed somewhat greater sensitivity than the SRT. These observations have been reported in previous studies, suggesting the data collected in this study was representative of a typical MS clinical sample.

Use of the Composite endpoint in a drug development clinical trial is preferable to methodologies used in past drug studies and current clinical practice. The Composite endpoint also is preferable to the large battery of tests administered by Fischer et al in English speaking subjects from the Avonex® phase 3 trial in regard to practicality, and also to the subset of tests identified in that research as sensitive to change in MS in regard to availability of alternate forms and validation of component subtests (Fischer. Annals of neurology. 2000; 48(6):885-92). Further, the Composite has psychometric support for combination of component subtests which was not the case in the Fischer et al., research which was guided by clinical judgment. Given further research support and the specific nature of the research question being investigated, use of the Composite might be preferred to the use of current clinical batteries such the MACFIMS and BRB ((Benedict RH. The Clinical neuropsychologist. 2002; 16(3):381-97); Rao S M. Neurology. 1991; 41:695-1)). That is, while the MACFIMS might serve well as a comprehensive assessment in clinical settings, it is far lengthier and has only one alternate form. It is noted that 3 of the 4 tests included in the current Composite endpoint are included in the MACFIMS, identifying the Composite endpoint as an alternative potentially more suitable for international multi-center pharmaceutical trials in MS due to its relative brevity, repeatability, and its status as a single outcome. In further support of the acceptability of the subtests comprising the Composite is the selection of some of its components by both BICAMS and the NINDS CDE Task Force (Langdon D W. Multiple sclerosis. 2012; 18(6): 891-8). Finally, the subtest components of the proposed Composite are easily administered by trained study personnel and not just by neuropsychologists, facilitating feasibility in large international clinical trials. For example, in the current study, test administrators included trained and supervised psychology graduate students and nurses as well as neuropsychologists.

The poor correlations between patient- and informant-reported neuropsychological symptoms and objective performance on the Composite endpoint was not unexpected as previous researchers have made similar observations (Benedict R H. Multiple sclerosis. 2003; 9(1):95-101). This study showed, inter alia, first, RRMS subjects were clearly better able to perceive their neuropsychological symptoms, as their self-appraisals were moderately correlated with their overall performance, whereas self-appraisals of SPMS subjects consistently lacked meaningful association with their test performances. This is consistent with the observation that self-assessment and insight into symptoms worsens with the severity of cognitive impairment. Second, as has been noted previously, informants are reasonably accurate reporters of MS cognitive problems (Benedict R H. Multiple sclerosis. 2003; 9(1):95-101). Based on the present results, the proposed Composite Cognitive endpoint has a psychometric basis, sensitivity similar to a larger and broader battery of tests, a normal distribution of scores, and excellent test-retest reliability.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the worldwide web at tigr.org and/or the National Center for Biotechnology Information (NCBI) on the worldwide web at ncbi.nlm.nih.gov.

EQUIVALENTS

Those skilled in the art will recognize, or be able to ascertain using no more than routine experimentation, many equivalents to the specific embodiments of the invention described herein. Such equivalents are intended to be encompassed.

What is claimed is:

1. A method of treating or preventing multiple sclerosis (MS), in a subject having MS, or at risk of developing MS, comprising:
   acquiring a value of a composite parameter from the subject, said composite parameter comprising a first value for an attention and/or processing speed (PS) factor and a second value for a memory factor, wherein:
   (i) the first value is acquired by obtaining an average of scores from at least one assessment of one or both of complex scanning or visual tracking, and at least one or two assessment(s) of processing speed, flexibility or calculation ability, and
   (ii) the second value is acquired by obtaining an average of scores from at least one or two assessments indicative of verbal learning and delayed recall, combined with at least one or two assessments indicative of visual learning and delayed recall; and
   responsive to said value, administering to the subject an MS therapy in an amount sufficient to reduce one or more symptoms associated with MS,
   wherein, in response to an increased value of said composite parameter relative to a reference value, the MS therapy is initiated or continued; and
   wherein, in response to a decreased value of said composite parameter relative to a reference value, the MS therapy is modified or an alternative MS therapy is used.

2. The method of claim 1, wherein the first value is obtained by one or both of:
   (i) as a function of a score based on a Symbol Digit Modalities Test (SMDT)) and a score based on at least one or two Paced Auditory Serial Addition Test (PASAT); or
   (ii) calculating the first value using the following equation:

{SMDT score+[PASAT 3 score+PASAT 2 score]/2)}/2.

3. The method of claim 2, wherein the value of the composite parameter comprises a score value chosen from one or more of: −0.6 to −1.6 for SDMT, −0.2 to −1.2 for PASAT 3, −0.12 to −1.12 for PASAT 2, −0.25 to −1.25 for SRT Total, −0.3 to −1.3 for SRT Delay, −0.8 to −1.8 for BVMT-R Total, or −1.2 to −2.2 for BVMTR Delay.

4. The method of claim 1, wherein the second value is obtained by one or both of:
   (i) averaging the scores at least one or two components of a Selective Reminding Test (SRT) and at least one or two components of a Brief Visuospatial memory Test (BVMT); or
   (ii) calculating the second value using the following equation:

[SRT learning score+SRT delay score+BVMT learning score and BVMT delay score]/4.

5. The method of claim 1, wherein the first and the second values are weighed equally or differentially in generating the value of the composite parameter.

6. The method of claim 1, wherein the scores from the assessments used to obtain the second value are weighed equally or differentially.

7. The method of claim 1, wherein the scores from the assessments are weighed equally or differentially, wherein the assessments are selected from the group consisting of:
   (i) verbal and visual memory;
   (ii) learning and delayed recall components; and
   (iii) complex scanning and/or visual tracking, and the at least one or two assessment(s) of processing speed, flexibility and/or calculation ability.

8. The method of claim 1, wherein the reference value is acquired from:
   a healthy subject or an average of healthy subjects;
   the subject prior to, during, or after the MS therapy;
   the subject at two, three or more time intervals; or
   at least two or more MS patients having the same or different disease progressions.

9. The method of claim 1, wherein the subject is monitored in one or more of the following periods: prior to beginning of treatment; during the treatment; after the treatment has been administered; or at a first and second time point at least months apart.

10. The method of claim 1, wherein the value of the composite parameter has a reliability of at least 0.65 or higher.

11. The method of claim 10, wherein the value of the composite parameter has a reliability of at least 0.85 or higher.

12. The method of claim 1, wherein an increase in the value of the composite parameter, relative to the reference value, by at least 5% or 0.2 to 1.5 SD, or more is indicative of improved cognitive function in the subject or wherein a decrease in the value of the composite parameter, relative to the reference value, by at least 5%, or 0.2 to 1.5 SD, or more is indicative of decreased cognitive function in the subject.

13. The method of claim 12, wherein an increase in the value of the composite parameter, relative to the reference value, by at least 20%, or more is indicative of improved cognitive function in the subject; or
   wherein a decrease in the value of the composite parameter, relative to the reference value, by at least 20%, or more is indicative of decreased cognitive function in the subject.

14. The method of claim 1, wherein the value of the composite parameter is lower in a patient having secondary progressive multiple sclerosis (SPMS) compared to a patient with relapse remitting multiple sclerosis (RRMS).

15. The method of claim 1, wherein the subject is a patient having one of: benign MS, relapse/remitting MS (RRMS), primary progressive MS, secondary progressive MS (SPMS), clinically isolated syndrome (CIS), or clinically defined MS (CDMS).

16. The method of claim 1, further comprising one or more steps of: performing a neurological examination, evaluating the subject's status on the Expanded Disability Status Scale (EDSS), or detecting the subject's lesion status as assessed using an MRI.

17. The method of claim 1, wherein the MS therapy comprises one or more of an IFN-β1 molecule; a polymer of glutamic acid, lysine, alanine and tyrosine; an antibody or fragment thereof against alpha-4 integrin; an anthracenedione molecule; a fingolimod; a dimethyl fumarate; an antibody to the alpha subunit of the IL-2 receptor of T cells; an antibody against CD52 or alemtuzumab; an inhibitor of a dihydroorotate dehydrogenase or teriflunomide; or an anti-LINGO-1 antibody.

18. The method of claim 17, wherein the IFN-β 1 molecule comprises one or more of an IFN-β1a or IFN-β 1b polypeptide, a variant, a homologue, a fragment or a pegylated variant thereof.

19. The method of claim 1, wherein the MS therapy comprises an IFN-1b molecule; a polymer of glutamic acid, lysine, alanine and tyrosine; or the MS therapy comprises an alternative MS therapy chosen from an antibody or fragment thereof against alpha-4 integrin; a dimethyl fumarate; an anthracenedione molecule; a fingolimod; a dimethyl fumarate; an antibody to the alpha subunit of the IL-2 receptor of T cells; or an anti-LINGO-1 antibody.

20. A method of evaluating and/or quantifying cognitive function in a subject having multiple sclerosis (MS), or at risk of developing MS, comprising:
  acquiring a value of a composite parameter from the subject, said composite parameter comprising a first value for an attention and/or processing speed (PS) factor and a second value for a memory factor, wherein:
    (i) the first value is acquired by obtaining an average of scores from at least one assessment of complex scanning or visual tracking or both, and at least one or two assessment(s) of processing speed, flexibility or calculation ability, and
    (ii) the second value is acquired by obtaining an average of scores from at least one or two assessments indicative of verbal learning and delayed recall, combined with at least one or two assessments indicative of visual learning and delayed recall; and
  comparing the value of the composite parameter from the subject to a reference value,
  wherein an increase in the value of the composite parameter, relative to a reference value, is indicative of improved cognitive function in the subject, and
  wherein a decrease in the value of the composite parameter, relative to a reference value, is indicative of decreased cognitive function in the subject.

* * * * *